(12) United States Patent
Kim et al.

(10) Patent No.: US 12,194,007 B2
(45) Date of Patent: Jan. 14, 2025

(54) PHARMACEUTICAL COMPOSITION FOR PREVENTING OR TREATING CANCER, COMPRISING GOSSYPOL, PHENFORMIN, AND ANTICANCER AGENT

(71) Applicant: National Cancer Center, Goyang-si (KR)

(72) Inventors: Soo Youl Kim, Goyang-si (KR); Jong Bae Park, Goyang-si (KR); Ho Lee, Goyang-si (KR); Hyon Chol Jang, Seoul (KR)

(73) Assignee: National Cancer Center, Gyeonggi-do (KR)

( * ) Notice: Subject to any disclaimer, the term of this patent is extended or adjusted under 35 U.S.C. 154(b) by 884 days.

(21) Appl. No.: 17/259,013

(22) PCT Filed: May 17, 2019

(86) PCT No.: PCT/KR2019/005913
§ 371 (c)(1),
(2) Date: Jan. 8, 2021

(87) PCT Pub. No.: WO2020/013435
PCT Pub. Date: Jan. 16, 2020

(65) Prior Publication Data
US 2021/0290570 A1 Sep. 23, 2021

(30) Foreign Application Priority Data
Jul. 9, 2018 (KR) .......................... 10-2018-0079490

(51) Int. Cl.
| | | |
|---|---|---|
| *A61K 31/155* | (2006.01) |
| *A61K 31/11* | (2006.01) |
| *A61K 31/337* | (2006.01) |
| *A61K 31/437* | (2006.01) |
| *A61K 31/44* | (2006.01) |
| *A61K 31/4745* | (2006.01) |
| *A61K 31/704* | (2006.01) |
| *A61K 33/243* | (2019.01) |
| *A61P 35/00* | (2006.01) |

(52) U.S. Cl.
CPC ............ *A61K 31/155* (2013.01); *A61K 31/11* (2013.01); *A61K 31/337* (2013.01); *A61K 31/437* (2013.01); *A61K 31/44* (2013.01); *A61K 31/4745* (2013.01); *A61K 31/704* (2013.01); *A61K 33/243* (2019.01); *A61P 35/00* (2018.01)

(58) Field of Classification Search
None
See application file for complete search history.

(56) References Cited

U.S. PATENT DOCUMENTS

| | | | |
|---|---|---|---|
| 7,432,304 B2 | 10/2008 | Wang et al. | |
| 8,945,627 B2 | 2/2015 | Kwon et al. | |
| 10,646,460 B2 | 5/2020 | Kang et al. | |
| 2011/0070232 A1 | 3/2011 | LePage et al. | |
| 2014/0343347 A1 | 11/2014 | Thompson et al. | |
| 2017/0071877 A1* | 3/2017 | Kim ....................... A61P 11/00 |
| 2019/0254995 A1 | 8/2019 | Kang et al. | |
| 2019/0388366 A1* | 12/2019 | Cheong ................. A61K 47/10 |

FOREIGN PATENT DOCUMENTS

| | | |
|---|---|---|
| KR | 10-2015-0102152 A | 9/2015 |
| KR | 10-2016-0094861 A | 8/2016 |
| KR | 10-2017-0097575 A | 8/2017 |
| WO | 2013019058 A2 | 2/2013 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Bailey et al., "Targeting the Metabolic Microenvironment of Tumors", Advances in Pharmacology, 2012, vol. 65, 63-107.
International Search Report mailed Aug. 23, 2019, in connection with International Application No. PCT/KR2019/005913, 7 pages.
Written Opinion mailed Aug. 23, 2019, in connection with International Application No. PCT/KR2019/005913, 5 pages.
Bauer et al., "Targeting Apoptosis to Overcome Cisplatin Resistance: A Translational Study in Head and Neck Cancer," International Journal of Radiation Oncology, Biology, Physics, 69(2), S106-S108 (2007).

* cited by examiner

*Primary Examiner* — Dale R Miller
(74) *Attorney, Agent, or Firm* — McDonnell Boehnen Hulbert & Berghoff LLP

(57) ABSTRACT

The present disclosure relates to a pharmaceutical composition comprising a combination of anticancer agents, capable of creating a synergistic effect when co-administer in the treatment of cancer, and more specifically, the present invention suggests anticancer agenst capable of creating a synergistic effect when co-administered with gossypol and phenformin. The anticancer agents selected as said anticancer agents in the present disclosure are sorafenib, vemurafenib, irinotecan, cisplatin, paclitaxel, and doxorubicin, and each of the aforementioned anticancer agent, when co-administered as a triple-drug combination with gossypol and phenformin can provide a significant synergistic effect in terms of the effect of suppressing the proliferation of cancer and killing cancer cell, compared to each mono-drug treatment group and a dual-drug treatment group of gossypol+phenformin.

15 Claims, 36 Drawing Sheets

PHARMACEUTICAL COMPOSITION FOR PREVENTING OR TREATING CANCER, COMPRISING GOSSYPOL, PHENFORMIN, AND ANTICANCER AGENT

CROSS-REFERENCE TO RELATED APPLICATIONS

This application is a U.S. National Stage entry of International Patent Application no. PCT/KR2019/005913, filed May 17, 2019, which claims the benefit of priority of Korean Patent Application no. 10-2018-0079490, filed Jul. 9, 2018.

TECHNICAL FIELD

The present disclosure relates to a pharmaceutical composition comprising a combination of anticancer agents, capable of exhibiting a synergistic effect through combined administration of an anticancer agent in treating cancer, and more specifically, suggests an anticancer agent capable of exhibiting a synergistic effect when treated in combination with gossypol and phenformin.

BACKGROUND ART

Cancer, unlike normal cells capable of proliferation and inhibition in a regularly restricted manner according to the needs of an individual, is a cell mass composed of undifferentiated cells that proliferate indefinitely, ignoring the necessary conditions in a tissue, and is also called a tumor. Cancer cells with this unlimited proliferation capacity infiltrate the surrounding tissues and, in more severe cases, metastasize to other organs of the body, resulting in severe pain and eventually death.

Cancer is largely classified into blood cancer and solid cancer, and occurs in almost all parts of the body such as pancreatic cancer, breast cancer, oral cancer, liver cancer, ovarian cancer, esophageal cancer, and skin cancer. As the above-mentioned cancer treatment method, a few targeted therapeutic agents such as Gleevec and Herceptin are recently used for treating specific cancers, but until now, the main methods are surgery, radiation therapy, and chemotherapy using chemotherapeutic agents that inhibit cell proliferation. However, since chemotherapeutic agents are not targeted therapeutic agents, the biggest problems with existing chemotherapeutic agents are side effects due to cytotoxicity and drug resistance, which are the main factors in which the treatment eventually fails despite the initial successful response by the anticancer agent. Therefore, to overcome the limitations of such chemotherapeutic agents, it is necessary to continuously develop targeted therapeutic agents with clear anticancer action mechanisms.

Various anticancer drugs have been developed and marketed through numerous studies. Among them, drugs that target the process of inhibiting cell proliferation and inducing apoptosis by blocking the ATP synthesis pathway in cancer cells are also being used. Gossypol and phenformin are known as anticancer compounds using such intracellular pathways (Korean Patent No. 10-1579371, Korean Patent No. 10-145806).

Gossypol, which is a naturally occurring double nonphenolic compound derived from *Gossypium* sp., is known as an inhibitor of aldehyde dehydrogenase (ALDH) in vivo, such as safrole or coumarins, and has been studied for its therapeutic use. Human trials of gossypol as male contraceptives have been reported to show that these compounds are safe for long-term administration.

Phenformin, which is a drug of the biguanide family such as metformin or buformin, is known as a therapeutic agent of diabetes. However, as biguanide-based drugs such as phenformin are known to be effective in the treatment of cancers lacking the p53 gene by activating AMP-activated protein kinase (AMPK), which is a key enzyme that physiologically regulates carbohydrate metabolism and lipid metabolism, studies on the anticancer effects of phenformin drugs have been conducted, and the potential for anticancer effects of phenformin has been demonstrated.

As described above, the anticancer effects of each of gossypol and phenformin are known, but it has not been reported that they can exhibit anticancer effect with a higher activity.

Therefore, the present inventors have tried to find a cancer treatment drug capable of exhibiting a synergistic anticancer effect even with a small dose, and as a result it was expected that a synergistic effect of each of anticancer agents could be exhibited through a combined administration of a triple-drug by mixing gossypol and phenformin with an anticancer agent. Thus, when sorafenib, vemurafenib, irinotecan, cisplatin, paclitaxel or doxorubicin was mixed together with gossypol and phenformin, an inhibitory effect of cancer cell proliferation and an inhibitory effect of cancer metastasis in various carcinomas were remarkably increased, and the level of growth inhibition of a xenografted tumor in a mouse model also exhibited a synergistic effect, and thus, the present disclosure has been completed by confirming that the triple drugs in which the anticancer agent selected in the present disclosure was mixed with gossypol and phenformin can be an active ingredient of a pharmaceutical composition for preventing or treating cancer.

DISCLOSURE

Technical Problem

Accordingly, an object of the present disclosure is to provide a pharmaceutical composition for preventing or treating cancer, which is capable of exhibiting a synergistic therapeutic effect according to mixing even when each anticancer agent is administered in a small dose.

Technical Solution

In order to achieve the above object, the present disclosure provides a pharmaceutical composition for preventing or treating cancer, comprising gossypol, phenformin and an anticancer agent as active ingredients.

In a preferred embodiment of the present disclosure, the anticancer agent may be any one of sorafenib, vemurafenib, irinotecan, cisplatin, paclitaxel, and doxorubicin.

In a preferred embodiment of the present disclosure, the gossypol may be a compound of the following Formula 1, and the phenformin may be a compound of the following Formula 2:

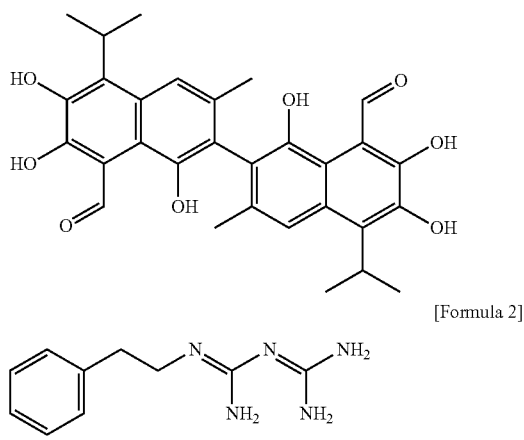

[Formula 1]

[Formula 2]

In a preferred embodiment of the present disclosure, the pharmaceutical composition may comprise gossypol, phenformin, and an anticancer agent mixed at a molar ratio of 0.1 to 10:10 to 500:1.

In a preferred embodiment of the present disclosure, the cancer may be one or more selected from the group consisting of kidney cancer, liver cancer, prostate cancer, melanoma, colon cancer, lung cancer, pancreatic cancer, ovarian cancer, breast cancer, stomach cancer, brain cancer, rectal cancer, blood cancer, and ovarian cancer.

Advantageous Effects

Accordingly, the present disclosure provides a pharmaceutical composition for preventing or treating cancer, comprising gossypol, phenformin and an anticancer agent as active ingredients. Anticancer agents selected in the present disclosure are sorafenib, vemurafenib, irinotecan, cisplatin, paclitaxel, and doxorubicin, and when treated with a triple drug combination by mixing them with gossypol and phenformin, respectively, significantly synergistic effect on cancer proliferation inhibitory effect and cancer cell killing effect compared to each single treatment group and double drug treatment group of gossypol+phenformin can be provided.

Therefore, in the case of treating cancer by using the pharmaceutical composition for preventing and treating cancer of the present disclosure, even a low concentration of drugs can exhibit significant cancer cell proliferation and tumor growth inhibitory effects, and thus is effective because they can specifically kill only cancer without affecting the survival of normal cells.

DESCRIPTION OF DRAWINGS

FIG. 9 shows the effect of reducing tumor growth in a triple combination group of gossypol, phenformin, and irinotecan in a mouse model of non-small cell lung cancer.

FIG. 9C is a diagram illustrating tumor weight in each drug administration group after completion of breeding.

FIGS. 11A-11C show an effect of reducing tumor growth in a triple combination group of gossypol, phenformin, and vemurafenib in a mouse model of melanoma, in which FIG. 11A is a diagram illustrating a change in tumor size according to the number of days of breeding:

FIG. 11B is a picture comparing tumor size in each drug administration group after completion of breeding: and FIG. 11C is a diagram illustrating tumor weight in each drug administration group after completion of breeding.

FIGS. 12A-12C show an effect of reducing tumor growth in a triple combination group of gossypol, phenformin, and irinotecan in a mouse model of stomach cancer, in which FIG. 12A is a diagram illustrating a change in tumor size according to the number of days of breeding.

FIG. 12B is a picture comparing tumor size in each drug administration group after completion of breeding.

FIG. 12C is a diagram illustrating tumor weight in each drug administration group after completion of breeding.

FIGS. 13A-13C show the effect of reducing tumor growth in a triple combination group of gossypol, phenformin, and doxorubicin in a mouse model of prostate cancer, in which FIG. 13A is a diagram illustrating a change in tumor size according to the number of days of breeding:

FIG. 13B is a picture comparing tumor size in each drug administration group after completion of breeding: and FIG. 13C is a diagram illustrating tumor weight in each drug administration group after completion of breeding.

BEST MODE

Figure 1A:
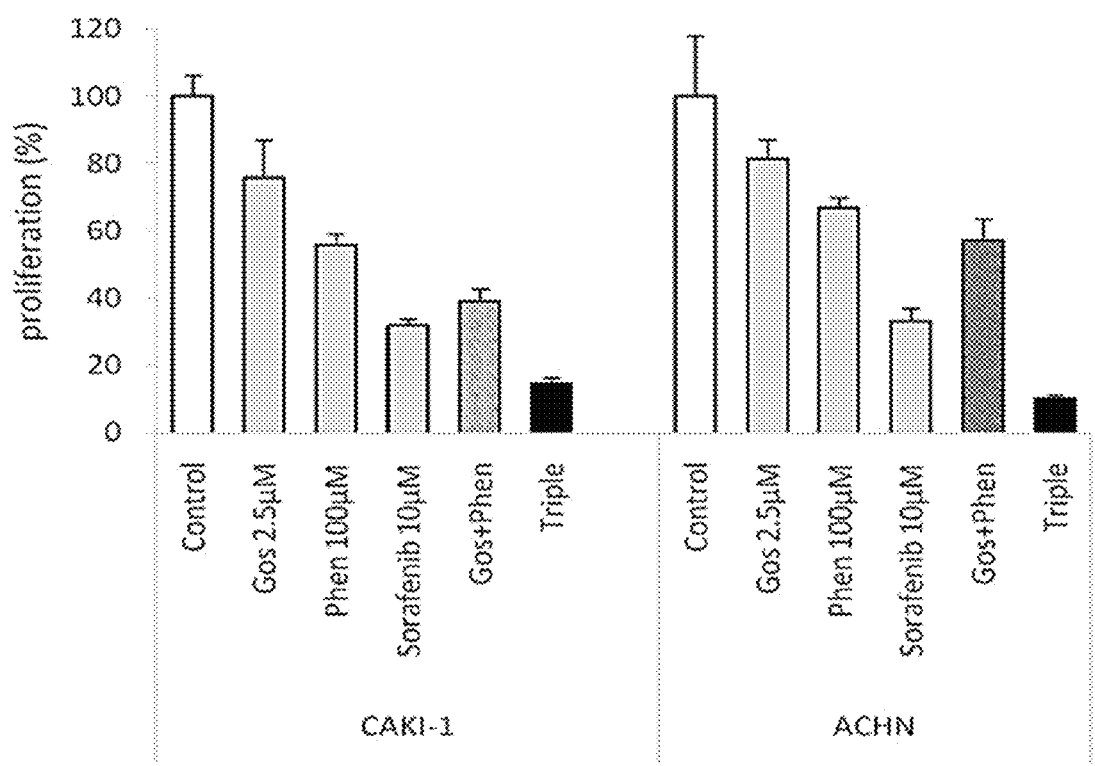
FIGS. 1A to 1C show a synergistic effect of inhibiting cell proliferation by a combination treatment of gossypol, phenformin, and an anticancer agent (sorafenib, sunitinib, or pazopanib) in a kidney cancer cell line.

The present disclosure provides a pharmaceutical composition for preventing or treating cancer, comprising gossypol, phenformin and an anticancer agent as active ingredients, wherein the anticancer agent is any one of sorafenib, vemurafenib, irinotecan, cisplatin, paclitaxel, and doxorubicin.

Mode for Disclosure

Hereinafter, the present disclosure will be provided in more detail.

The present disclosure provides a pharmaceutical composition for preventing or treating cancer, comprising gossypol, phenformin and an anticancer agent as active ingredients, wherein the anticancer agent is any one of sorafenib, vemurafenib, irinotecan, cisplatin, paclitaxel, and doxorubicin.

"Gossypol" of the composition provided by the present disclosure acts as an inhibitor of ALDH expression and activity in cells. Specifically, in the cellular mechanism in which ALDH produces NDAH in an intracellular serine-folate mechanism and ATP is produced therefrom, gossypol acts as an inhibitor of ALDH expression and activity, causing ATP deficiency in the cell and killing the cancer cell. The gossypol has a structure of the following Formula 1:

[Formula 1]

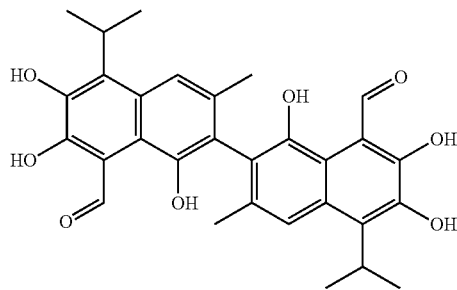

The "phenformin" of the composition provided by the present disclosure acts as an inhibitor of mitochondrial complex I in cells. Specifically, phenformin may reduce mitochondrial membrane potential through inhibition of mitochondrial complex I activity, and as a result, the synthesis of intracellular ATP is reduced, so that cancer cells may be effectively killed. The phenformin has a structure of the following Formula 2:

[Formula 2]

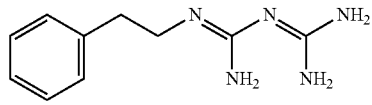

As the gossypol and phenformin contained as active ingredients of the composition provided by the present disclosure, all ranges of equivalents recognized by those skilled in the art as pharmaceutically exhibiting the same or similar level of effect may be included. Specifically, the gossypol and phenformin may be used by selecting a pharmaceutically acceptable salt, hydrate or solvate thereof.

That is, the gossypol is an inhibitor of ALDH expression and activity, and serves to cause ATP deficiency in cells to kill cancer cells, and the phenformin is an inhibitor of mitochondrial complex I, and may exhibit a synergistic effect of ATP deficiency by reducing mitochondrial membrane potential. Thus, an increased cancer growth inhibitory effect can be expected through a combination treatment of gossypol and phenformin. The present disclosure provides an anticancer agent composition capable of exhibiting a more synergistic effect in inhibiting cancer cell growth by adding a combination of the anticancer agents as well as the gossypol and phenformin.

Specifically, the present disclosure provides any one of sorafenib, vemurafenib, irinotecan, cisplatin, paclitaxel, and doxorubicin as an anticancer agent. In a specific embodiment of the present disclosure, the present inventors treated kidney cancer, melanoma, colon cancer, non-small cell lung cancer, breast cancer, ovarian cancer, prostate cancer, liver cancer and stomach cancer cell lines in combination with a mixture of various anticancer agents in addition to gossypol and phenformin, and selected only an anticancer agent exhibiting a synergistic effect thereby.

More specifically, the sorafenib is known as a kinase inhibitor that can be mainly used in the treatment of kidney cancer, liver cancer, and prostate cancer, etc. The sorafenib is a small molecule inhibitor of VEGFR, PDGFR and Raf family kinase, which are various tyrosine protein kinases.

In addition, the vemurafenib is a compound named as an abbreviation for V600E mutated BRAF inhibition, and is an inhibitor of B-Raf enzyme. The vemurafenib is an anticancer agent mainly used for the treatment of end-stage melanoma, and is known as being able to represent a specific therapeutic effect for about 60% of melanoma patients in V600E BRAF mutant melanoma.

Irinotecan is an anticancer agent widely used in the treatment of colon cancer, small cell lung cancer, and pancreatic cancer, and is an anticancer agent known as being able to induce synergistic effects through combination treatment mainly by mixing with other anticancer agents. The irinotecan is known as acting as an inhibitor of topoisomerase by blocking the activity of topoisomerase 1 in cancer cells, thereby exerting DNA destruction and cell death effects.

Cisplatin is an anticancer agent used for the treatment of testicular cancer, bladder cancer, ovarian cancer, prostate cancer, and head and neck cancer. Cisplatin is known as inducing cell disruption and cell death by inhibiting the DNA synthesis of cancer cells with reacting specifically to the DNA of cancer cells and forming cross-links between or within the DNA chains.

Paclitaxel is a drug used as a therapeutic agent for various cancers such as ovarian cancer, breast cancer, lung cancer and pancreatic cancer. The paclitaxel plays a role in inhibiting cell growth by affecting the formation of microtubes during cell division, but it is known that side effects such as hair loss, inhibition of bone marrow function, allergic reactions, muscle pain and lung inflammation appear.

Doxorubicin is a type of antibiotic produced by *Streptomyces peucetius* var. *caesius*, and is an anticancer agent used by showing anticancer effects against malignant lymphoma, breast cancer, and lung cancer. When the doxorubicin is inserted between the DNA base pairs of cancer cells, it is known to inhibit topoisomerase II activity, and reactions of RNA polymerase and DNA polymerase, and to cleave single-stranded DNA chains.

The pharmaceutical composition of the present disclosure can obtain a significant synergistic effect in the effect of inhibiting cancer proliferation and inducing death by administering the gossypol, the phenformin, and the anticancer agent in combination. At this time, gossypol, phenformin, and an anticancer agent may be mixed at a molar ratio of 0.1 to 10:10 to 500:1, and specifically a molar ratio of 1 to 7:50 to 200:1 is preferable. From the viewpoint of obtaining a significant cancer prevention and treatment effect by using a small concentration of anticancer agent through the pharmaceutical composition of the present disclosure, it is more preferable that the gossypol and phenformin are mixed at a molar ratio of 2.5 to 5:100:1.

More specifically, the pharmaceutical composition of the present disclosure may comprise the selected anticancer agent at a concentration of 20 nM to 10 µM, and at this time, the concentration of the gossypol and phenformin may be mixed in the mixing ratio above. That is, the gossypol may be selectively used by one skilled in the art in a concentration range of 0.002 µM to 100 µM, preferably 0.02 µM to 70 µM, more preferably 0.05 to 50 µM. In addition, the phenformin may be mixed in the mixing ratio above and may be selectively used by one skilled in the art in a concentration range of 0.2 µM to 5 mM, preferably 1 µM to 2 mM, more preferably 2 µM to 1 mM.

In the pharmaceutical composition of the present disclosure, the "cancer" is preferably any one or more selected from the group consisting of kidney cancer, liver cancer, prostate cancer, melanoma, colon cancer, lung cancer, pancreatic cancer, ovarian cancer, breast cancer, stomach cancer, brain cancer, rectal cancer, blood cancer, and ovarian cancer, but is limited thereto. Specifically, the cancer is preferably any one or more selected from the group consisting of kidney cancer, liver cancer, prostate cancer, melanoma, colon cancer, lung cancer, pancreatic cancer, breast cancer and colon cancer, but is limited thereto. In addition, the cancer preferably includes cancer stem cells, but is not limited thereto.

More specifically, when the "cancer" is "kidney cancer", the pharmaceutical composition of the present disclosure is preferable because the use of the combination with gossypol, phenformin, and sorafenib may exhibit a synergistic effect on preventing or treating cancer. If the sorafenib is not used and the sunitinib or pazopanib is combined, a significant synergistic effect is not exhibited, and the effect of the combination treatment will not be desirable.

When the "cancer" is "melanoma", the pharmaceutical composition of the present disclosure is preferable because the use of the combination with gossypol, phenformin, and vemurafenib may exhibit a synergistic effect on preventing or treating cancer. If the vemurafenib is not used and the cisplatin or oxaliplatin is combined, a significant synergistic effect is not exhibited, and the effect of the combination treatment will not be desirable.

When the "cancer" is "colon cancer", the pharmaceutical composition of the present disclosure is preferable because the use of the combination with gossypol, phenformin, and irrinotecan may exhibit a synergistic effect on preventing or treating cancer. If the irinotecan is not used and the cisplatin or capecitabin is combined, a significant synergistic effect is not exhibited, and the effect of the combination treatment will not be desirable.

When the "cancer" is "lung cancer", the pharmaceutical composition of the present disclosure is preferable because the use of the combination with gossypol, phenformin, and irrinotecan may exhibit a synergistic effect on preventing or treating cancer. If the irinotecan is not used and the cisplatin or 5-FU is combined, a significant synergistic effect is not exhibited, and the effect of the combination treatment will not be desirable.

When the "cancer" is "breast cancer", the pharmaceutical composition of the present disclosure is preferable because the use of the combination with gossypol, phenformin, and paclitaxel may exhibit a synergistic effect on preventing or treating cancer. If the paclitaxel is not used and the cisplatin or doxorubicin is combined, a significant synergistic effect is not exhibited, and the effect of the combination treatment will not be desirable.

When the "cancer" is "ovarian cancer", the pharmaceutical composition of the present disclosure is preferable because the use of the combination with gossypol, phenformin, and cisplatin may exhibit a synergistic effect on preventing or treating cancer. If the cisplatin is not used and the paclitaxel or irinotecan is combined, a significant synergistic effect is not exhibited, and the effect of the combination treatment will not be desirable.

When the "cancer" is "prostate cancer", the pharmaceutical composition of the present disclosure is preferable because the use of the combination with gossypol, phenformin, and doxorubicin may exhibit a synergistic effect on preventing or treating cancer. If the doxorubicin is not used and the docetaxel or irinotecan is combined, a significant synergistic effect is not exhibited, and the effect of the combination treatment will not be desirable.

When the "cancer" is "liver cancer", the pharmaceutical composition of the present disclosure is preferable because the use of the combination with gossypol, phenformin, and cisplatin may exhibit a synergistic effect on preventing or treating cancer. If the cisplatin is not used and sorafenib is combined, a significant synergistic effect is not exhibited, and the effect of the combination treatment will not be desirable.

When the "cancer" is "stomach cancer", the pharmaceutical composition of the present disclosure is preferable because the use of the combination with gossypol, phenformin, and irinotecan may exhibit a synergistic effect on preventing or treating cancer.

When the composition of the present disclosure is used as a medicine, the pharmaceutical composition comprising the gossypol, phenformin, and anticancer agent of the present disclosure may be formulated and administered in various oral or parenteral dosage forms as described below at the time of clinical administration, but is not limited thereto.

Formulations for oral administration include, for example, tablets, pills, hard/soft capsules, solutions, suspensions, emulsifiers, syrups, granules, elixirs, and the like, and the formulations comprise diluents (e.g., lactose, dextrose, sucrose, mannitol, sorbitol, cellulose and/or glycine), lubricants (e.g., silica, talc, stearic acid and its magnesium or calcium salts and/or polyethylene glycol) in addition to the active ingredients. Tablets may also contain binders such as magnesium aluminum silicate, starch paste, gelatin, methylcellulose, sodium carboxymethylcellulose and/or polyvinylpyrrolidine, optionally such as starch, agar, disintegrants such as alginic acid or sodium salts thereof, or boiling mixtures and/or absorbents, colorants, flavors, and sweeteners.

The pharmaceutical composition comprising gossypol, phenformin and an anticancer agent of the present disclosure may be administered parenterally, and parenteral administration is a method of infusing a subcutaneous injection, an intravenous injection, an intramuscular injection, or an intrathoracic injection. At this time, in order to formulate a formulation for parenteral administration, gossypol, phenformin and an anticancer agent are mixed in water together with a stabilizer or buffer to prepare a solution or suspension, which can be prepared in a unit dosage form of ampoules or vials. The composition may be sterilized and/or contain adjuvants such as preservatives, stabilizers, hydrating agents or emulsification accelerators, salts and/or buffers for controlling osmotic pressure, and other therapeutically useful substances, and may be formulated according to mixing, granulation or coating that are conventional methods.

In addition, the dosage of the pharmaceutical composition containing gossypol, phenformin, and an anticancer agent of the present disclosure to the human body may vary depending on the patient's age, weight, sex, dosage form, health condition and degree of disease, and based on an adult patient having weight of 60 kg, is generally 0.001 to 1,000 mg/day, preferably 0.01 to 500 mg/day, and may also be administered in divided doses once a day or several times a day at regular time intervals according to the judgment of a doctor or pharmacist.

Hereinafter, the present disclosure will be described in more detail through examples. These examples are for illustrative purposes only, and it will be apparent to those of ordinary skill in the art that the scope of the present disclosure is not construed as being limited by these examples.

Example 1

Screening of Anticancer Agents that Show Synergistic Effects in Renal Cell Carcinoma by a Combination Treatment with Gossypol and Phenformin In the present disclosure, it was attempted to screen a combination of anticancer agents capable of exhibiting a synergistic effect of anticancer action when mixed and treated with conventional anticancer agents. Accordingly, an anticancer agent was selected to increase the anticancer effect by a triple combination obtained by mixing additional anticancer agents in addition to gossypol and phenformin. First, the sorafenib, sunitinib, and pazopanib as candidate anticancer agents in addition to the gossypol and phenformin in order to select a combination capable of exhibiting a synergistic effect of anticancer action on kidney cancer were selected as each subject.

Specifically, while culturing the ACHN cell line or CAKI-1 cell line, which is a kidney cancer cell line, each cell was inoculated into a 96-well plate at a density of 5,000 to 20,000 cells/well depending on the amplification phase of the culture time. After inoculation, the anticancer agent mixtures of the following [Table 1] to [Table 3] were added to each well and cultured in a $CO_2$ incubator for 24 hours. The anticancer agent mixture was prepared so that the final concentration of each anticancer agent can be appropriately added by mixing each at a stock concentration and then adding 100 µl each. After treatment with the anticancer agent, cells were further cultured for 48 hours, and then 10% (w/v) trichloroacetic acid (TCA) was added to each well and incubated at 4° C. for 60 minutes to fix the cells. The supernatant liquid other than the fixed cells was removed, the plate was washed 5 times with tap water, and then dried in air. After drying, 100 µl of 0.4% (w/v) sulforhodamine B buffer solution containing 1% acetic acid was added to each well, and left at room temperature for 5 minutes to stain the cells. After staining the cells, the cells were washed 5 times with 1% acetic acid to remove unstained dye and then dried in air. The colored dye was immobilized with 10 mM trizma base, and then absorbance was measured at 515 nm using a plate reader. As an untreated control, the degree of cell proliferation of a cell line cultured without treatment with an anticancer agent was measured, and the degree of cell proliferation of each experimental group with respect to the untreated control was calculated as a relative ratio and expressed as a percentage (%).

TABLE 1

Design of a triple drug treatment group experiment containing sorafenib (FIG. 1A)

| Number | Sample name | Anticancer agent (µM) | | |
|---|---|---|---|---|
| 1 | Single treatment group with gossypol | Gossypol (2.5 µM) | — | — |
| 2 | Single treatment group with phenformin | — | Phenformin (100 µM) | — |
| 3 | Single treatment group with sorafenib | — | — | Sorafenib (10 µM) |
| 4 | Double drug treatment group | Gossypol (2.5 µM) | Phenformin (100 µM) | — |
| 5 | Triple drug treatment group | Gossypol (2.5 µM) | Phenformin (100 µM) | Sorafenib (10 µM) |

TABLE 2

Figure 1B:
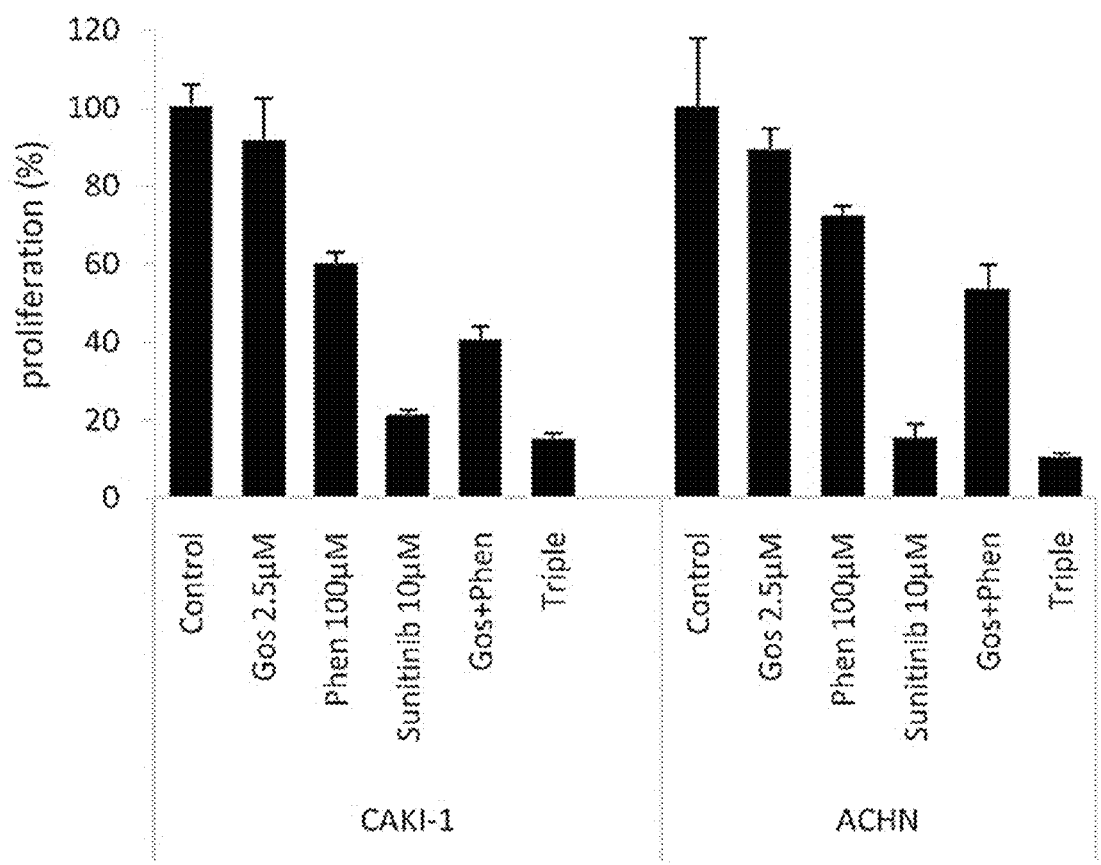

Design of a triple drug treatment group experiment containing sunitinib (FIG. 1B)

| Number | Sample name | Anticancer agent (µM) | | |
|---|---|---|---|---|
| 1 | Single treatment group with gossypol | Gossypol (2.5 µM) | — | — |
| 2 | Single treatment group with phenformin | — | Phenformin (100 µM) | — |
| 3 | Single treatment group with sunitinib | — | — | Sunitinib (10 µM) |
| 4 | Double drug treatment group | Gossypol (2.5 µM) | Phenformin (100 µM) | — |
| 5 | Triple drug treatment group | Gossypol (2.5 µM) | Phenformin (100 µM) | Sunitinib (10 µM) |

TABLE 3

Figure 1C:
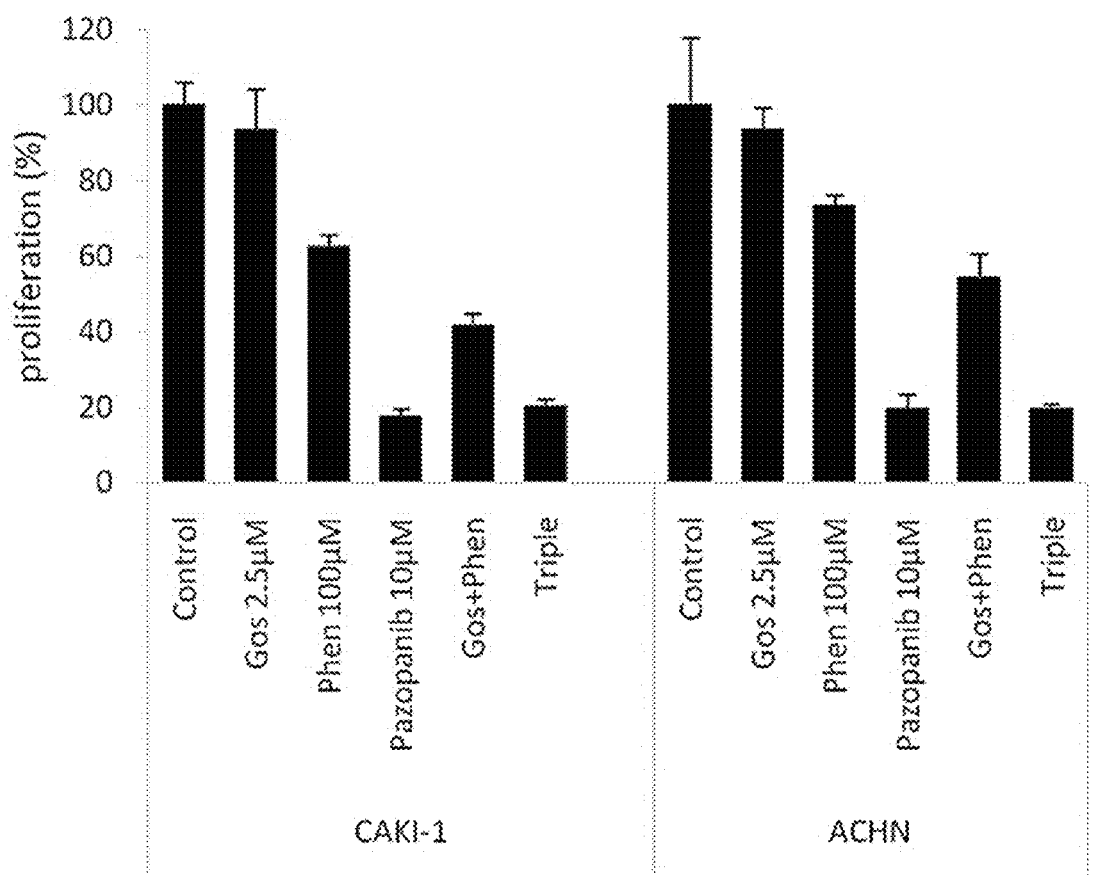

Design of a triple drug treatment group experiment containing pazopanib (FIG. 1C)

| Number | Sample name | Anticancer agent (µM) | | |
|---|---|---|---|---|
| 1 | Single treatment group with gossypol | Gossypol (2.5 µM) | — | — |
| 2 | Single treatment group with phenformin | — | Phenformin (100 µM) | — |
| 3 | Single treatment group with sorafenib | — | — | Pazopanib (10 µM) |
| 4 | Double drug treatment group | Gossypol (2.5 µM) | Phenformin (100 µM) | — |
| 5 | Triple drug treatment group | Gossypol (2.5 µM) | Phenformin (100 µM) | Pazopanib (10 µM) |

As a result, first, as shown in FIG. 1A, it was confirmed that the proliferation of cancer cells could be inhibited when each renal cell carcinoma was treated with each anticancer agent such as gossypol, phenformin, or sorafenib alone. In addition, the double drug treatment group of gossypol and phenformin showed a similar level of cell proliferation inhibitory effect to the group treated with sorafenib alone, and in particular, the triple drug treatment group in which gossypol, phenformin, and sorafenib were mixed was confirmed that the cell proliferation level was significantly suppressed compared to the case of single or double drug treatment with each anticancer agent, and thus it was confirmed that sorafenib can exhibit a synergistic effect of anticancer action when mixed with gossypol and phenformin (FIG. 1A). In contrast, as shown in FIGS. 1B and 1C, it was confirmed that since sunitinib (FIG. 1B) and pazopanib (FIG. 1C) in the triple drug treatment group show only an effect of inhibiting cell proliferation in a level similar to that of the double drug treatment group, the synergistic effect of the anticancer action by treatment with triple drugs was not exhibited.

Example 2

Screening of Anticancer Agents that Show Synergistic Effects in Melanoma by Combination Treatment with Gossypol and Phenformin In order to select a combination capable of exhibiting a synergistic effect of anticancer action on melanoma, vemurafenib (PLX032), cisplatin, and oxaliplatin as candidate anticancer agents in addition to gossypol and phenformin were selected as each subject.

Specifically, a UACC62 cell line or an A375 cell line as the melanoma cell line was each cultured, the same method as in [Example 1] was performed and it was confirmed whether the synergistic effect of the anticancer action was exhibited by the mixed administration of the anticancer agents disclosed in [Table 4] to [Table 6] as cell growth in melanoma cells is inhibited, through SRB analysis.

TABLE 4

Figure 2A:
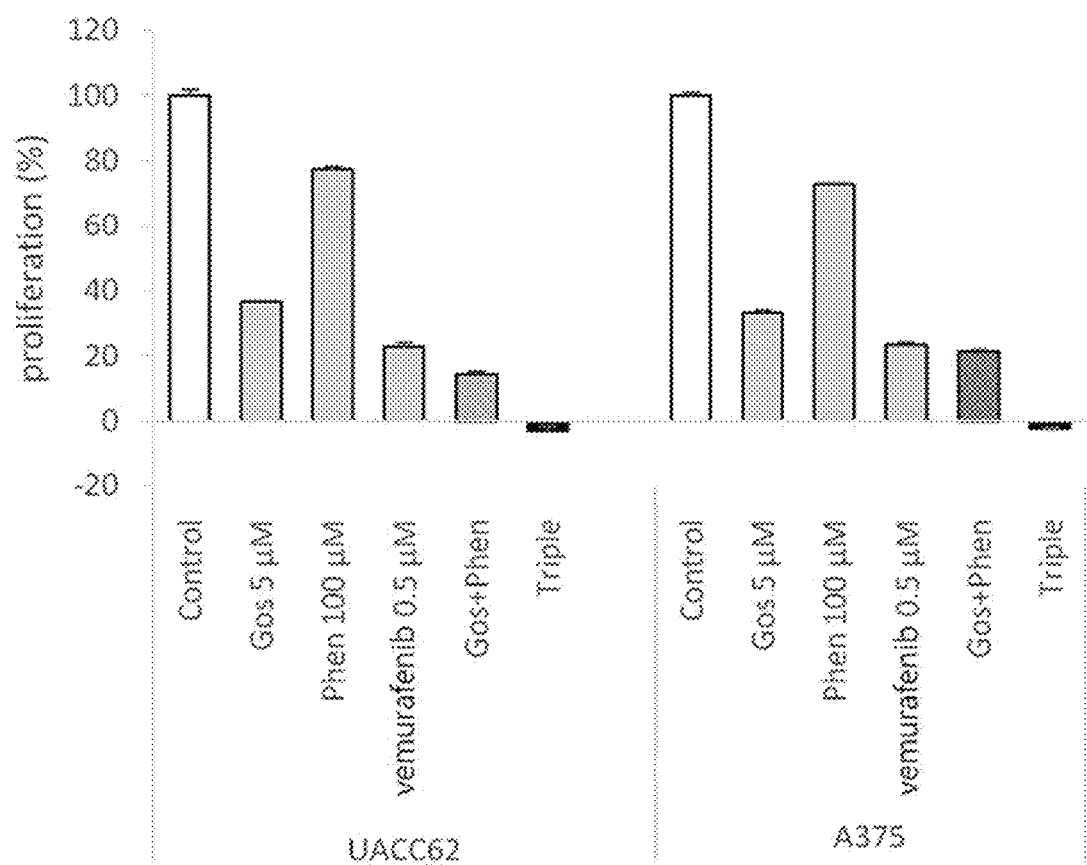
FIGS. 2A to 2C show a synergistic effect of inhibiting cell proliferation by a combination treatment of gossypol, phenformin, and an anticancer agent (vemurafenib, cisplatin, or oxaliplatin) in a melanoma cell line.

Design of a triple drug treatment group experiment containing vemurafenib (FIG. 2A)

| Number | Sample name | Anticancer agent (μM) | | |
|---|---|---|---|---|
| 1 | Single treatment group with gossypol | Gossypol (5 μM) | — | — |
| 2 | Single treatment group with phenformin | — | Phenformin (100 μM) | — |
| 3 | Single treatment group with vemurafenib | — | — | Vemurafenib (0.5 μM) |
| 4 | Double drug treatment group | Gossypol (5 μM) | Phenformin (100 μM) | — |
| 5 | Triple drug treatment group | Gossypol (5 μM) | Phenformin (100 μM) | Vemurafenib (0.5 μM) |

TABLE 5

Figure 2B:
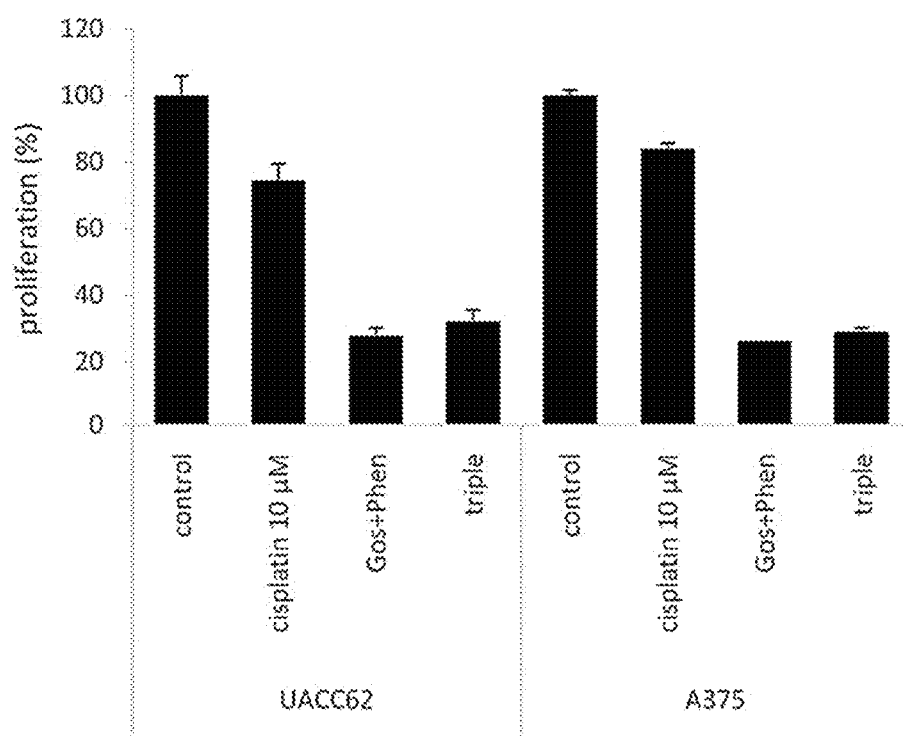

Design of a triple drug treatment group experiment containing cisplatin (FIG. 2B)

| Number | Sample name | Anticancer agent (μM) | | |
|---|---|---|---|---|
| 1 | Double drug treatment group | Gossypol (5 μM) | Phenformin (100 μM) | — |
| 2 | Single treatment group with cisplatin | — | — | Cisplatin (10 μM) |
| 3 | Triple drug treatment group | Gossypol (5 μM) | Phenformin (100 μM) | Cisplatin (10 M) |

TABLE 6

Figure 2C:
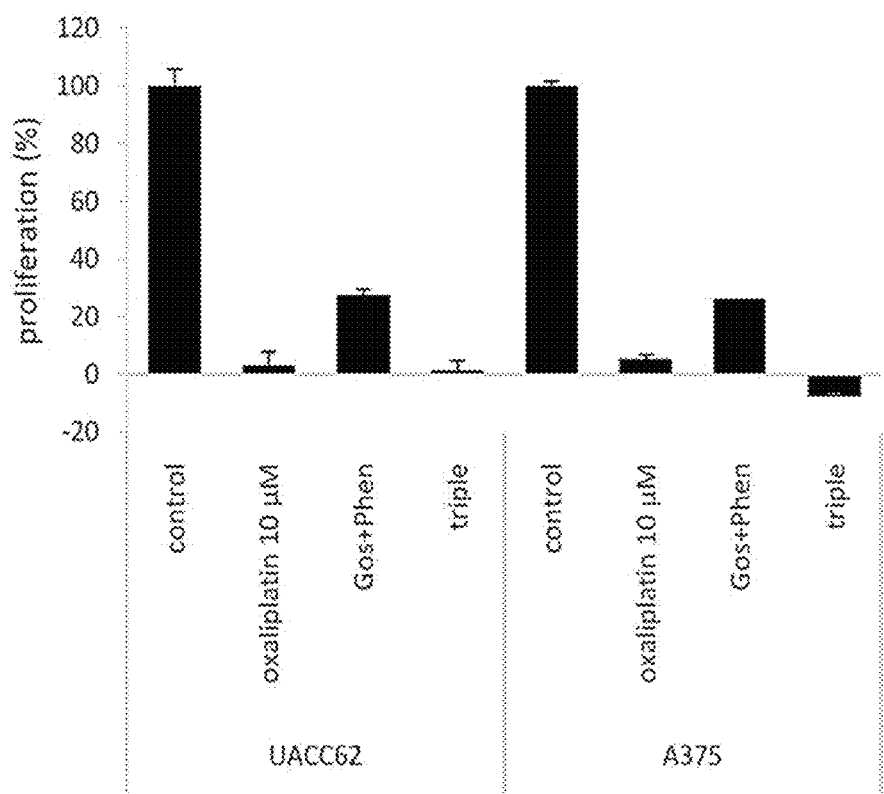

Design of a triple drug treatment group experiment containing oxaliplatin (FIG. 2C)

| Number | Sample name | Anticancer agent (μM) | | |
|---|---|---|---|---|
| 1 | Double drug treatment group | Gossypol (5 μM) | Phenformin (100 μM) | — |
| 2 | Single treatment group with oxaliplatin | — | — | Oxaliplatin (10 μM) |
| 3 | Triple drug treatment group | Gossypol (5 μM) | Phenformin (100 μM) | Oxaliplatin (10 μM) |

As a result, first, as shown in FIG. 2A, it was confirmed that the proliferation of cancer cells could be inhibited at a significant level when each melanoma cell was treated with both a single treatment group of gossypol, phenformin, or vemurafenib and a double drug treatment group of gossypol and phenformin. However, in particular, it was confirmed that in the triple drug treatment group in which gossypol, phenformin, and vemurafenib were mixed, the cell proliferation level was significantly suppressed compared to the case of single or double drug treatment with each anticancer agent, and thus it was confirmed that vemurafenib can exhibit a synergistic effect of anticancer action when mixed with gossypol and phenformin (FIG. 2A).

In contrast, as shown in FIGS. 2B and 2C, it was confirmed that since cisplatin (FIG. 2B) and oxaliplatin (FIG. 2C) in the triple drug treatment group exhibited only an effect of inhibiting cell proliferation in a level similar to that of the double drug treatment group, the synergistic effect of the anticancer action by treatment with triple drugs was not exhibited.

Example 3

Screening of Anticancer Agents that Show Synergistic Effects in Colorectal Cancer by Combination Treatment with Gossypol and Phenformin In order to select a combination capable of exhibiting a synergistic effect of anticancer action on colorectal cancer, irinotecan, cisplatin, and capecitabin as candidate anticancer agents in addition to gossypol and phenformin were selected as each subject.

Specifically, HT29 cell line or Colo205 cell line as the colorectal cancer cell line was each cultured, and the same method as in [Example 1] was performed and it was confirmed whether the synergistic effect of the anticancer action was exhibited by the mixed administration of the anticancer agents disclosed in [Table 7] to [Table 9] as cell growth in colorectal cancer cells is inhibited, through SRB analysis.

TABLE 7

Figure 3A:
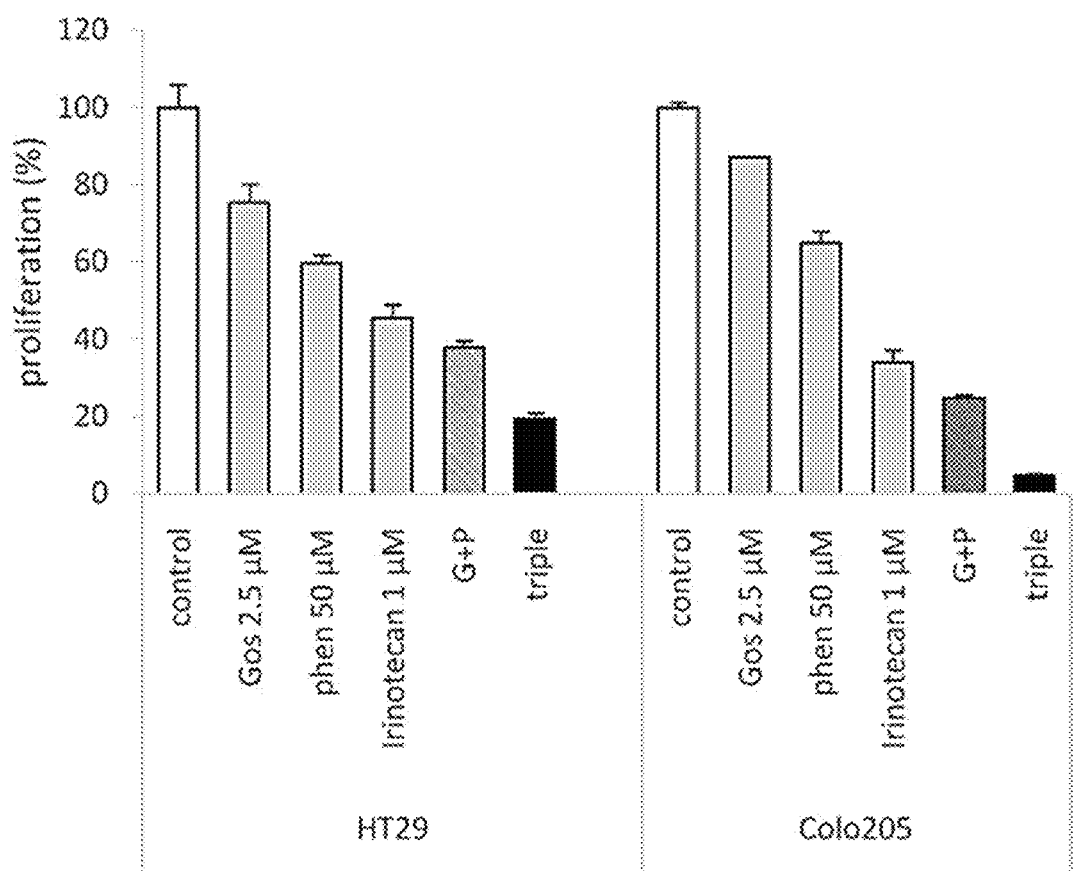
FIGS. 3A to 3C show a synergistic effect of inhibiting cell proliferation by a combination treatment of gossypol, phenformin, and an anticancer agent (irinotecan, cisplatin, or capecitabine) in a colon cancer cell line.

Design of a triple drug treatment group experiment containing irinotecan (FIG. 3A)

| Number | Sample name | Anticancer agent (μM) | | |
|---|---|---|---|---|
| 1 | Single treatment group with gossypol | Gossypol (2.5 μM) | — | — |
| 2 | Single treatment group with phenformin | — | Phenformin (50 μM) | — |
| 3 | Single treatment group with irinotecan | — | — | Irinotecan (1 μM) |

TABLE 7-continued

Design of a triple drug treatment group
experiment containing irinotecan (FIG. 3A)

| Number | Sample name | Anticancer agent (μM) | | |
|---|---|---|---|---|
| 4 | Double drug treatment group | Gossypol (2.5 μM) | Phenformin (50 μM) | — |
| 5 | Triple drug treatment group | Gossypol (2.5 μM) | Phenformin (50 μM) | Irinotecan (1 μM) |

TABLE 8

Figure 3B:
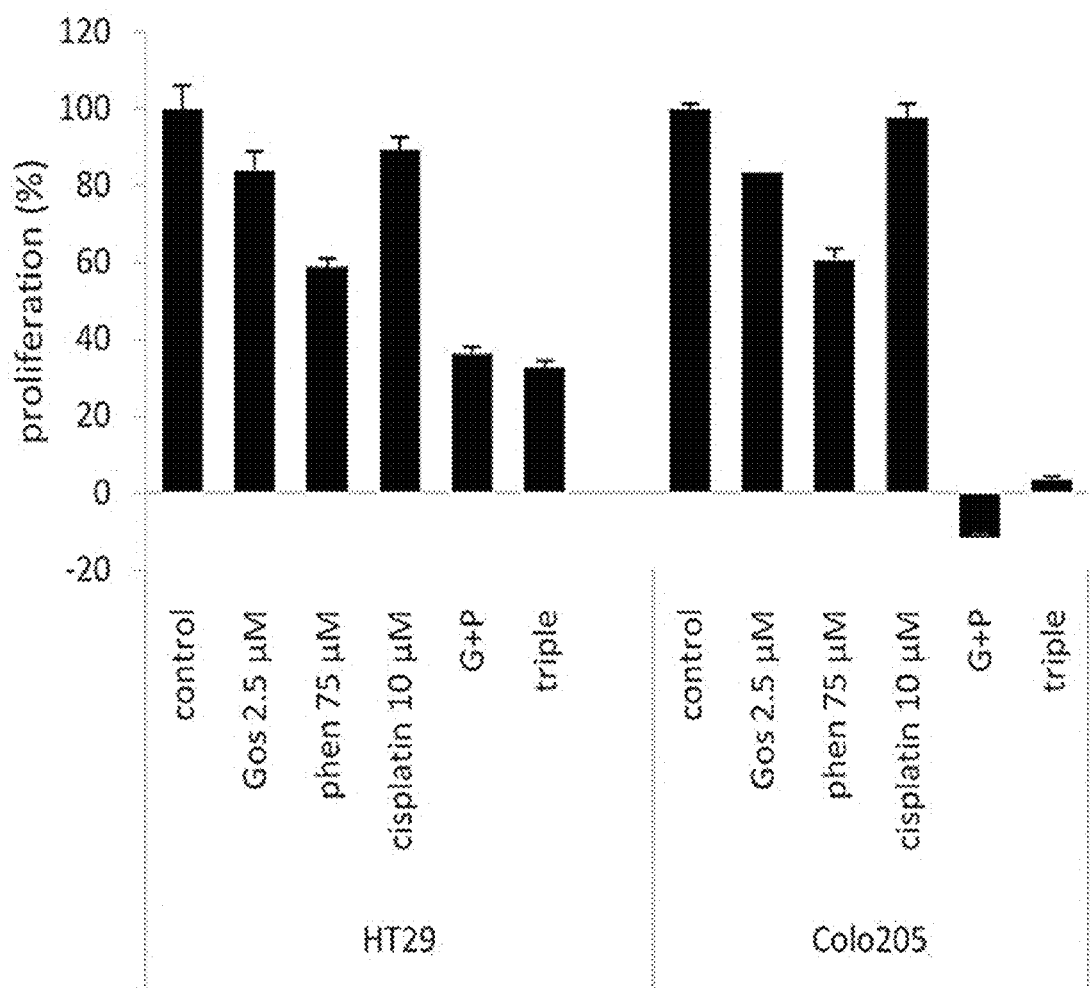

Design of a triple drug treatment group
experiment containing cisplatin (FIG. 3B)

| Number | Sample name | Anticancer agent (μM) | | |
|---|---|---|---|---|
| 1 | Single treatment group with gossypol | Gossypol (2.5 μM) | — | — |
| 2 | Single treatment group with phenformin | — | Phenformin (75 μM) | — |
| 3 | Single treatment group with cisplatin | — | — | Cisplatin (10 μM) |
| 4 | Double drug treatment group | Gossypol (2.5 μM) | Phenformin (75 μM) | — |
| 5 | Triple drug treatment group | Gossypol (2.5 μM) | Phenformin (75 μM) | Cisplatin (10 μM) |

TABLE 9

Figure 3C:
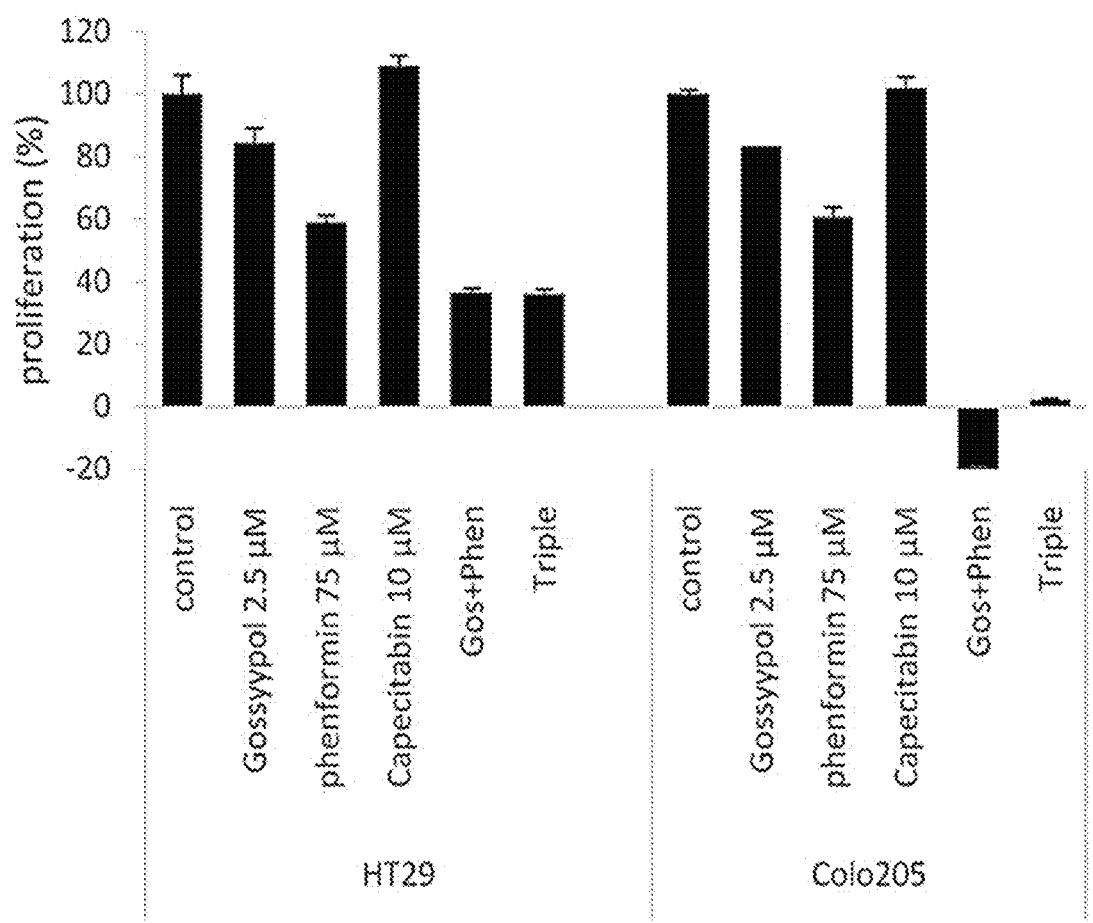

Design of a triple drug treatment group
experiment containing capecitabine (FIG. 3C)

| Number | Sample name | Anticancer agent (μM) | | |
|---|---|---|---|---|
| 1 | Single treatment group with gossypol | Gossypol (2.5 μM) | — | — |
| 2 | Single treatment group with phenformin | — | Phenformin (75 μM) | — |
| 3 | Single treatment group with capecitabine | — | — | Capecitabine (10 μM) |
| 4 | Double drug treatment group | Gossypol (2.5 μM) | Phenformin (75 μM) | — |
| 5 | Triple drug treatment group | Gossypol (2.5 μM) | Phenformin (75 μM) | Capecitabine (10 μM) |

As a result, first, as shown in FIG. 3A, it was confirmed that the proliferation of cancer cells could be inhibited at a significant level when each colorectal cell was treated with both a single treatment group of gossypol, phenformin, or irinotecan and a double drug treatment group of gossypol and phenformin. However, in particular, it was confirmed that in the triple drug treatment group in which gossypol, phenformin, and irinotecan are mixed, the cell proliferation level was significantly suppressed compared to the case of single or double drug treatment with each anticancer agent, and thus it was confirmed that irinotecan can exhibit a synergistic effect of anticancer action when mixed with gossypol and phenformin (FIG. 3A). In contrast, as shown in FIGS. 3B and 3C, it was confirmed that since cisplatin (FIG. 3B) and capecitabine (FIG. 3C) in the triple drug treatment group show only an effect of inhibiting cell proliferation in a level similar to that of the double drug treatment group, the synergistic effect of the anticancer action by treatment with triple drugs was not exhibited.

Example 4

Screening of Anticancer Agents that Show Synergistic Effects in Non-Small Cell Lung Cancer (NSCLC) by Combination Treatment with Gossypol and Phenformin In order to select a combination capable of exhibiting a synergistic effect of anticancer action on non-small cell lung cancer, irinotecan, cisplatin, and 5-fluorouracil (5-FU) as candidate anticancer agents in addition to gossypol and phenformin were selected as each subject.

Specifically, A549 cell line or H522 cell line as the non-small cell lung cancer cell line was each cultured, and the same method as in [Example 1] was performed and it was confirmed whether the synergistic effect of the anticancer action was exhibited by the mixed administration of the anticancer agents disclosed in [Table 10] to [Table 12] as cell growth in non-small cell lung cancer cells is inhibited, through SRB analysis.

TABLE 10

Figure 4A:
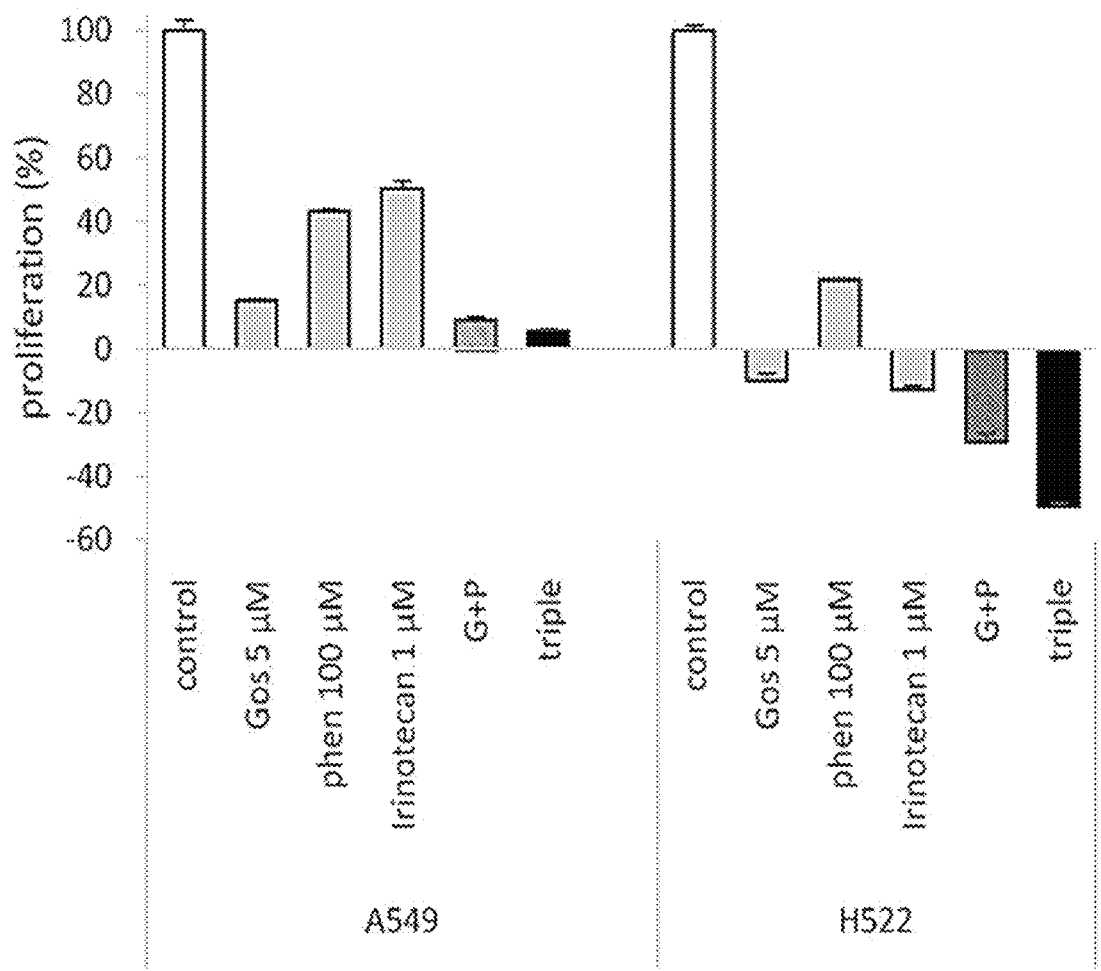
FIGS. 4A to 4C show a synergistic effect of inhibiting cell proliferation by a combination treatment of gossypol, phenformin, and an anticancer agent (irinotecan, cisplatin, or 5-FU) in a lung cancer cell line.

Design of a triple drug treatment group
experiment containing irinotecan (FIG. 4A)

| Number | Sample name | Anticancer agent (μM) | | |
|---|---|---|---|---|
| 1 | Single treatment group with gossypol | Gossypol (5 μM) | — | — |
| 2 | Single treatment group with phenformin | — | Phenformin (100 μM) | — |
| 3 | Single treatment group with irinotecan | — | — | Irinotecan (1 μM) |
| 4 | Double drug treatment group | Gossypol (5 μM) | Phenformin (100 μM) | — |
| 5 | Triple drug treatment group | Gossypol (5 μM) | Phenformin (100 μM) | Irinotecan (1 μM) |

TABLE 11

Figure 4B:
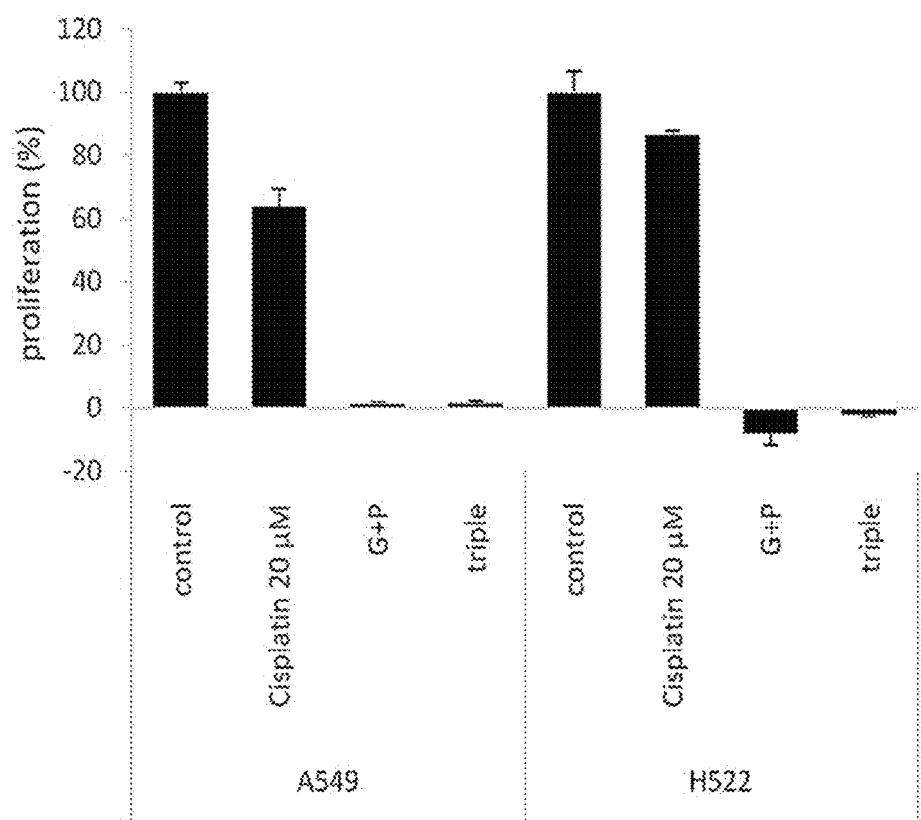

Design of a triple drug treatment group
experiment containing cisplatin (FIG. 4B)

| Number | Sample name | Anticancer agent (μM) | | |
|---|---|---|---|---|
| 1 | Double drug treatment group | Gossypol (5 μM) | Phenformin (100 μM) | — |
| 2 | Single treatment group with cisplatin | — | — | Cisplatin (20 μM) |
| 3 | Triple drug treatment group | Gossypol (5 μM) | Phenformin (100 μM) | Cisplatin (20 μM) |

TABLE 12

Figure 4C:
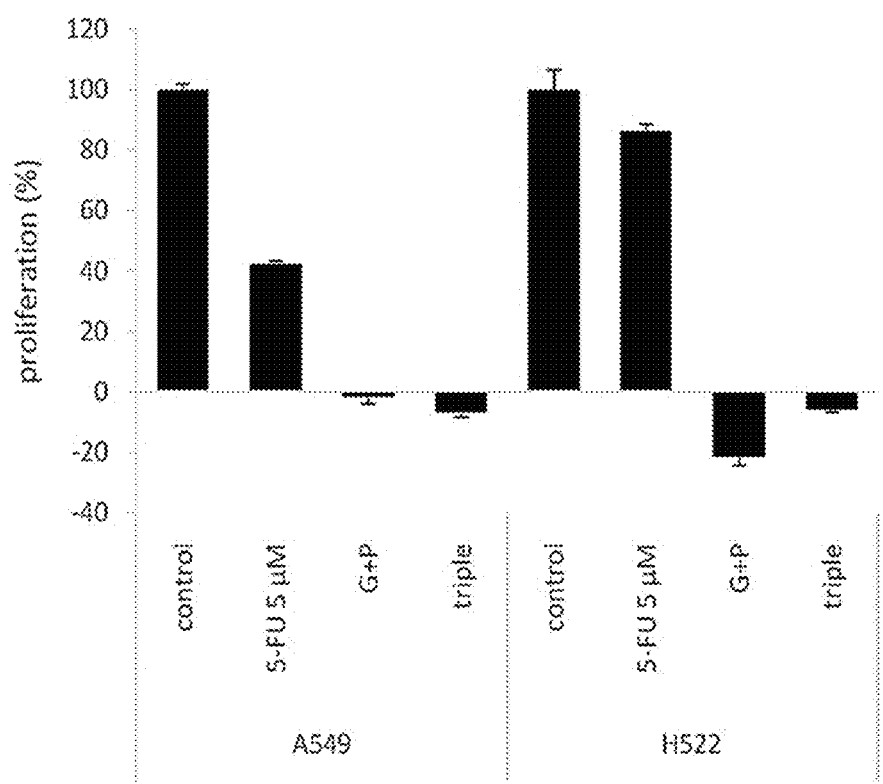

Design of a triple drug treatment group
experiment containing 5-FU (FIG. 4C)

| Number | Sample name | Anticancer agent (μM) | | |
|---|---|---|---|---|
| 1 | Double drug treatment group | Gossypol (5 μM) | Phenformin (100 μM) | — |
| 2 | Single treatment group with 5-FU | — | — | 5-FU (5 μM) |
| 3 | Triple drug treatment group | Gossypol (5 μM) | Phenformin (100 μM) | 5-FU (5 μM) |

As a result, first, as shown in FIG. 4A, it was confirmed that the proliferation of cancer cells could be inhibited at a significant level when each cell of non-small cell lung cancer (NSCLC) was treated with both a single treatment group of gossypol, phenformin, or irinotecan and a double drug treatment group of gossypol and phenformin. However, in particular, it was confirmed that in the triple drug treatment group in which gossypol, phenformin, and irinotecan were mixed, the cell proliferation level was significantly suppressed and the cell number was reduced to exhibit an effect of killing the cells, compared to the case of single or double drug treatment with each anticancer agent, and thus it was confirmed that irinotecan can exhibit a synergistic effect of anticancer action when mixed with gossypol and phenformin (FIG. 4A). In contrast, as shown in FIGS. 4B and 4C, it was confirmed that since cisplatin (FIG. 4B) and 5-FU (FIG. 4C) in the triple drug treatment group show only an effect of inhibiting cell proliferation in a level similar to that of the double drug treatment group, the synergistic effect of the anticancer action by treatment with triple drugs was not exhibited.

Example 5

Screening of Anticancer Agents that Show Synergistic Effects in Breast Cancer by Combination Treatment with Gossypol and Phenformin In order to select a combination capable of exhibiting a synergistic effect of anticancer action on breast cancer, paclitaxel, cisplatin, and doxorubicin as candidate anticancer agents in addition to gossypol and phenformin were selected as each subject.

Specifically, BT549 cell line or MB231 cell line as the breast cancer cell line was each cultured, and the same method as in [Example 1] was performed and it was confirmed whether the synergistic effect of the anticancer action was exhibited by the mixed administration of the anticancer agents disclosed in [Table 13] to [Table 15] as cell growth in the breast cancer cells is inhibited, through SRB analysis.

TABLE 13

Figure 5A:
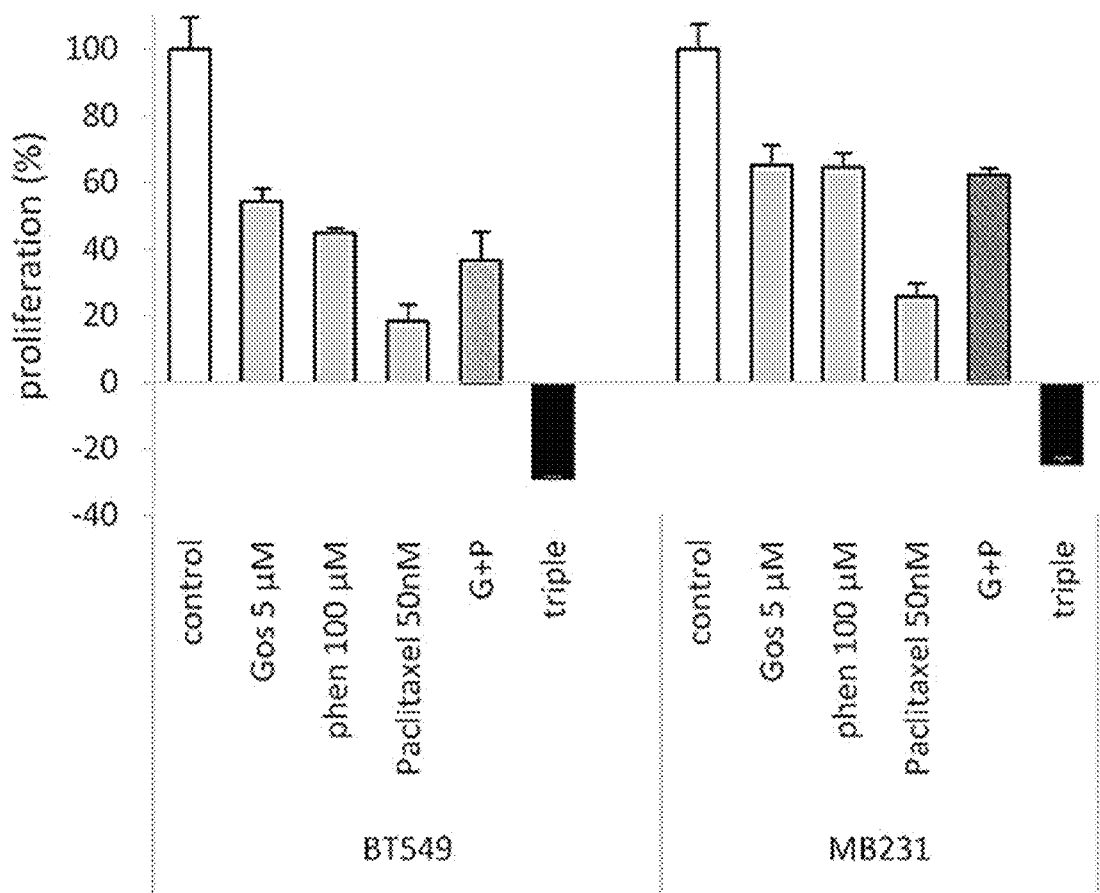
FIGS. 5A to 5C show a synergistic effect of inhibiting cell proliferation by a combination treatment of gossypol, phenformin, and an anticancer agent (paclitaxel, cisplatin, or doxorubicin) in a breast cancer cell line.

Design of a triple drug treatment group experiment containing paclitaxel (FIG. 5A)

| Number | Sample name | Anticancer agent (μM) | | |
|---|---|---|---|---|
| 1 | Single treatment group with gossypol | Gossypol (5 μM) | — | — |
| 2 | Single treatment group with phenformin | — | Phenformin (100 μM) | — |
| 3 | Single treatment group with paclitaxel | — | — | Paclitaxel (50 nM) |
| 4 | Double drug treatment group | Gossypol (5 μM) | Phenformin (100 μM) | — |
| 5 | Triple drug treatment group | Gossypol (5 μM) | Phenformin (100 μM) | Paclitaxel (50 nM) |

TABLE 14

Figure 5B:
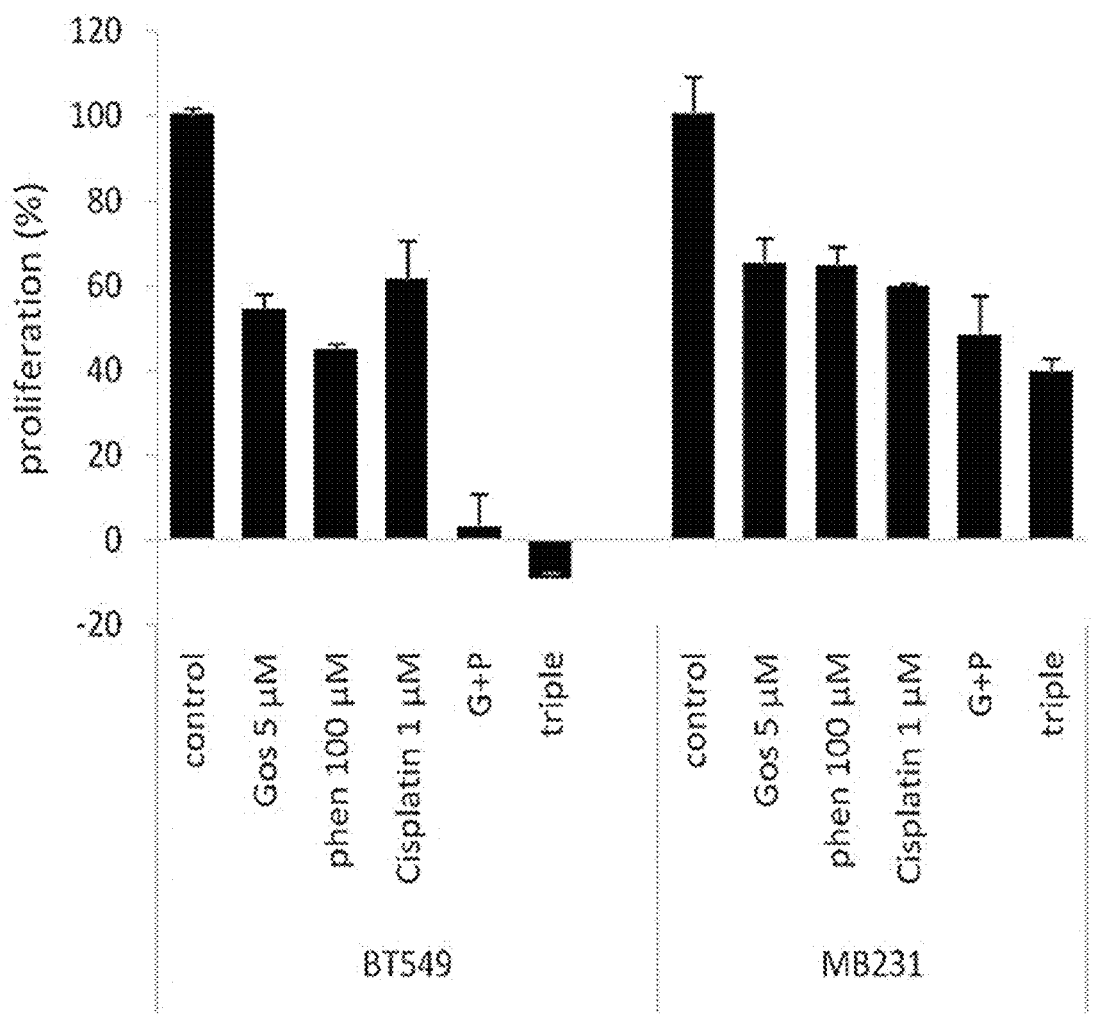

Design of a triple drug treatment group experiment containing cisplatin (FIG. 5B)

| Number | Sample name | Anticancer agent (μM) | | |
|---|---|---|---|---|
| 1 | Single treatment group with gossypol | Gossypol (5 μM) | — | — |
| 2 | Single treatment group with phenformin | — | Phenformin (100 μM) | — |
| 3 | Single treatment group with cisplatin | — | — | Cisplatin (1 μM) |
| 4 | Double drug treatment group | Gossypol (5 μM) | Phenformin (100 μM) | — |
| 5 | Triple drug treatment group | Gossypol (5 μM) | Phenformin (100 μM) | Cisplatin (1 μM) |

TABLE 15

Figure 5C:
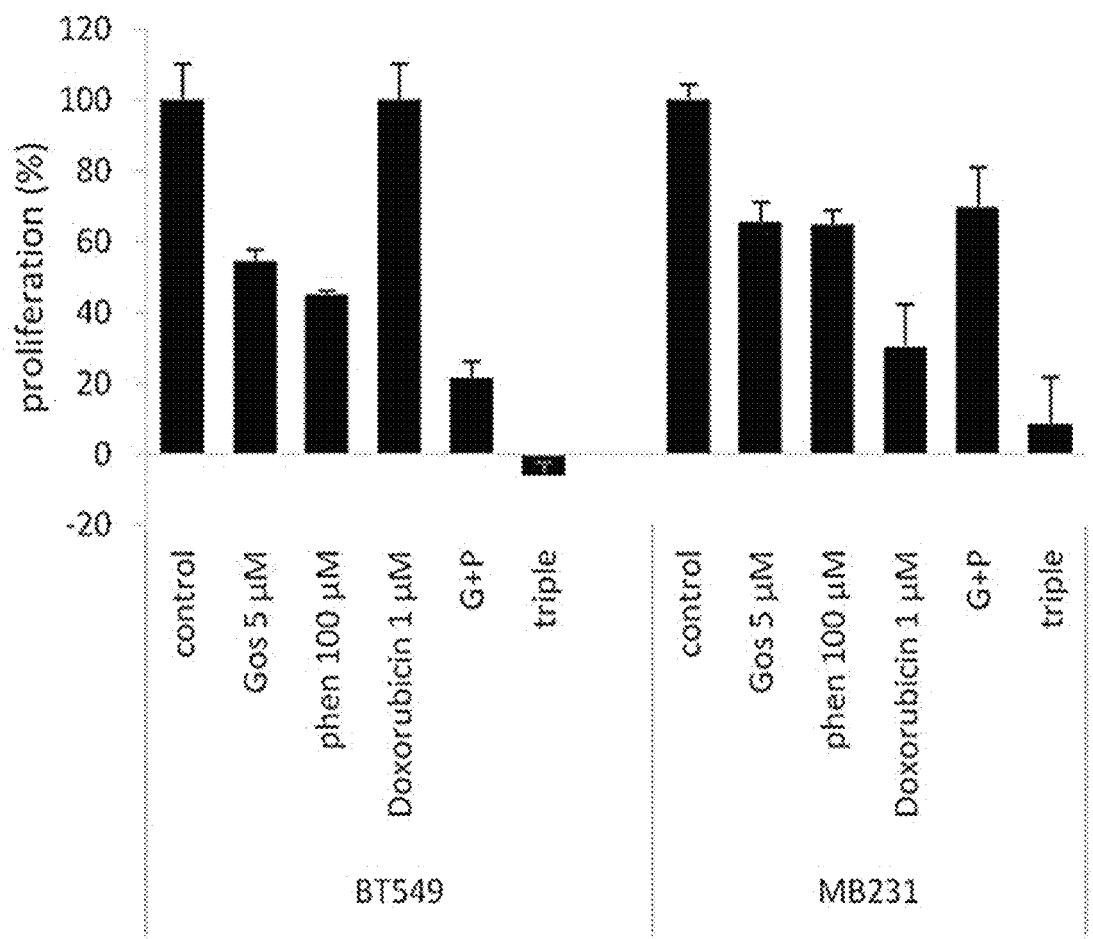

Design of a triple drug treatment group experiment containing doxorubicin (FIG. 5C)

| Number | Sample name | Anticancer agent (μM) | | |
|---|---|---|---|---|
| 1 | Single treatment group with gossypol | Gossypol (5 μM) | — | — |
| 2 | Single treatment group with phenformin | — | Phenformin (100 μM) | — |
| 3 | Single treatment group with doxorubicin | — | — | Doxorubicin (1 μM) |
| 4 | Double drug treatment group | Gossypol (5 μM) | Phenformin (100 μM) | — |
| 5 | Triple drug treatment group | Gossypol (5 μM) | Phenformin (100 μM) | Doxorubicin (1 μM) |

As a result, first, as shown in FIG. 5A, it was confirmed that the proliferation of cancer cells could be inhibited at a significant level when each breast cancer cell was treated with both a single treatment group of gossypol, phenformin, or irinotecan and a double drug treatment group of gossypol and phenformin. However, in particular, it was confirmed that in the triple drug treatment group in which gossypol, phenformin, and irinotecan were mixed, a cell proliferation level was significantly suppressed and the cell number was reduced to exhibit an effect of killing the cells, compared to the case of single or double drug treatment with each anticancer agent, and thus it was confirmed that irinotecan can exhibit a synergistic effect of anticancer action when mixed with gossypol and phenformin (FIG. 5A). In contrast, as shown in FIGS. 5B and 5C, it was confirmed that since cisplatin (FIG. 5B) and doxorubicin (FIG. 5C) in the triple drug treatment group show only an effect of inhibiting cell proliferation in a level similar to that of the double drug treatment group, the synergistic effect of the anticancer action by treatment with triple drugs was not exhibited.

Example 6

Screening of Anticancer Agents that Show Synergistic Effects in Ovarian Cancer by Combination Treatment with Gossypol and Phenformin In order to select a combination capable of exhibiting a synergistic effect of anticancer action on ovarian cancer, cisplatin, paclitaxel and irinotecan as candidate anticancer agents in addition to gossypol and phenformin were selected as each subject.

Specifically, SK-OV-3 or OVCAR3 cell line as the ovarian cancer cell line was each cultured, and the same method as in [Example 1] was performed and it was confirmed whether the synergistic effect of the anticancer action was exhibited by the mixed administration of the anticancer agents disclosed in [Table 16] to [Table 18] as cell growth in the ovarian cancer cells is inhibited, through SRB analysis.

TABLE 16

Figure 6A:
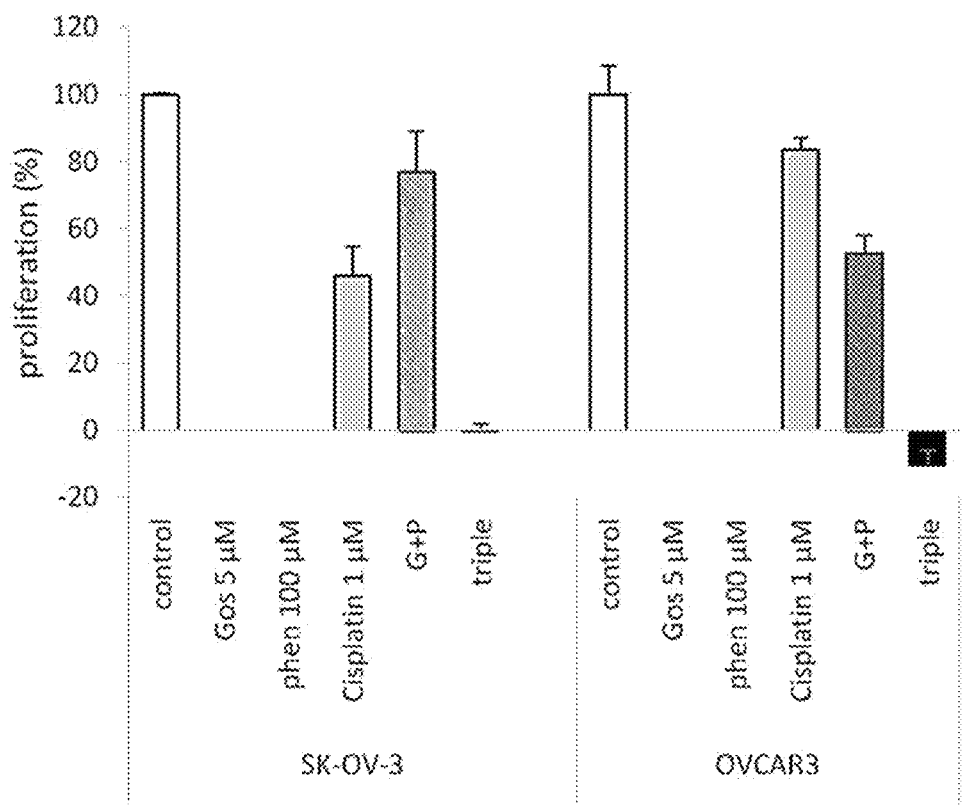
FIGS. 6A to 6C show a synergistic effect of inhibiting cell proliferation by a combination treatment of gossypol, phenformin, and an anticancer agent (cisplatin, paclitaxel, or irinotecan) in an ovarian cancer cell line.

Design of a triple drug treatment group experiment containing cisplatin (FIG. 6A)

| Number | Sample name | Anticancer agent (μM) | | |
|---|---|---|---|---|
| 1 | Single treatment group with gossypol | Gossypol (5 μM) | — | — |
| 2 | Single treatment group with phenformin | — | Phenformin (100 μM) | — |
| 3 | Single treatment group with cisplatin | — | — | Cisplatin (1 nM) |
| 4 | Double drug treatment group | Gossypol (5 μM) | Phenformin (100 μM) | — |
| 5 | Triple drug treatment group | Gossypol (5 μM) | Phenformin (100 μM) | Cisplatin (1 nM) |

TABLE 17

Figure 6B:
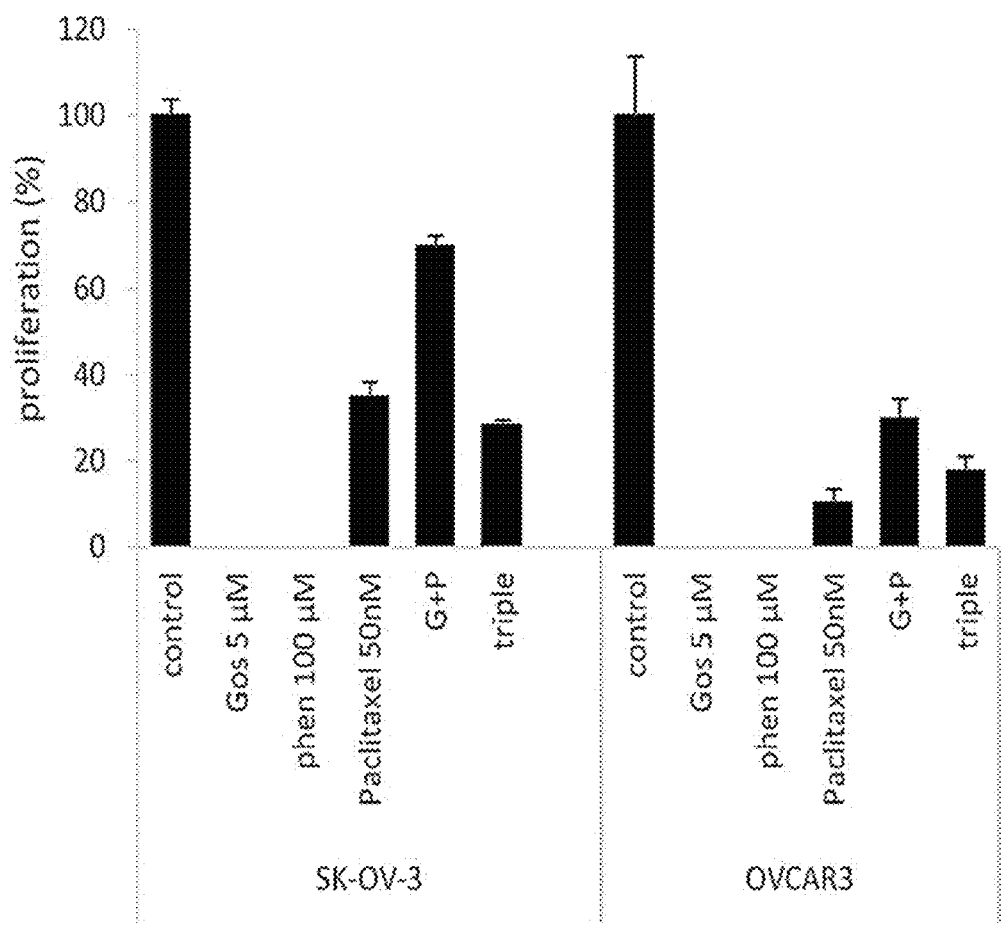

Design of a triple drug treatment group experiment containing paclitaxel (FIG. 6B)

| Number | Sample name | Anticancer agent (μM) | | |
|---|---|---|---|---|
| 1 | Single treatment group with gossypol | Gossypol (5 μM) | — | — |
| 2 | Single treatment group with phenformin | — | Phenformin (100 μM) | — |
| 3 | Single treatment group with paclitaxel | — | — | Paclitaxel (50 nM) |
| 4 | Double drug treatment group | Gossypol (5 μM) | Phenformin (100 μM) | — |
| 5 | Triple drug treatment group | Gossypol (5 μM) | Phenformin (100 μM) | Paclitaxel (50 nM) |

TABLE 18

Figure 6C:
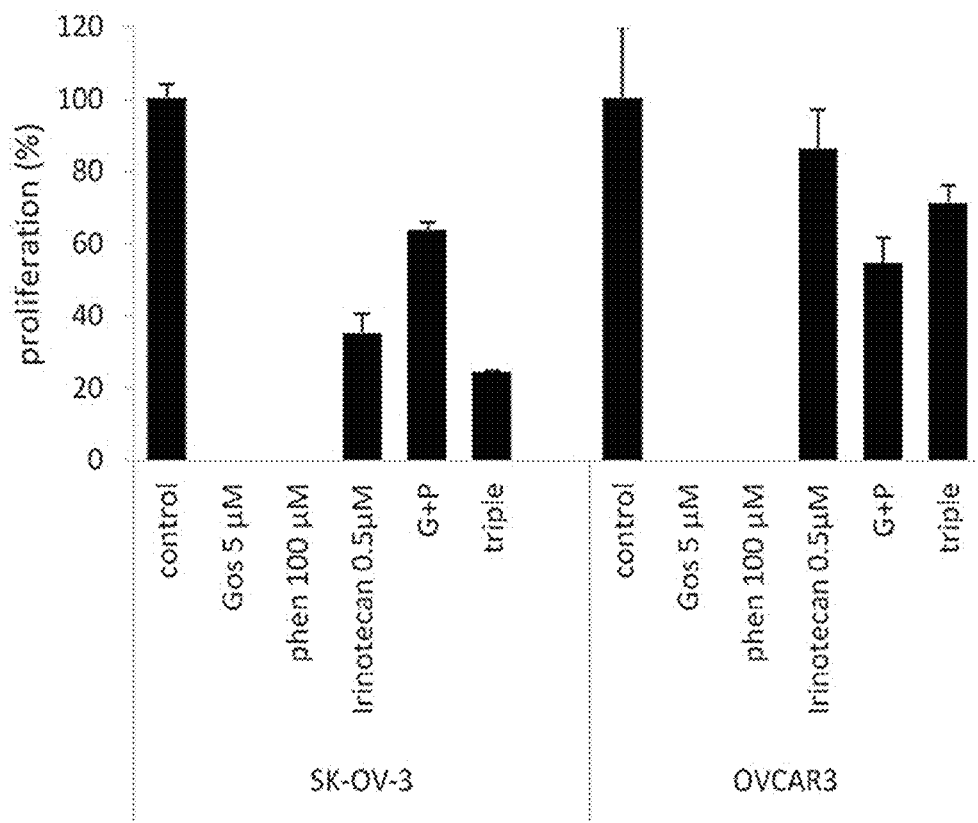

Design of a triple drug treatment group experiment containing irinotecan (FIG. 6C)

| Number | Sample name | Anticancer agent (μM) | | |
|---|---|---|---|---|
| 1 | Single treatment group with gossypol | Gossypol (5 μM) | — | — |
| 2 | Single treatment group with phenformin | — | Phenformin (100 μM) | — |
| 3 | Single treatment group with irinotecan | — | — | Irionotecan (0.5 μM) |
| 4 | Double drug treatment group | Gossypol (5 μM) | Phenformin (100 μM) | — |
| 5 | Triple drug treatment group | Gossypol (5 μM) | Phenformin (100 μM) | Irionotecan (0.5 μM) |

As a result, first, as shown in FIG. 6A, it was confirmed that the proliferation of cancer cells could be inhibited at a significant level when each ovarian cancer cell was treated with both a single treatment group of gossypol, phenformin, or cisplatin and in a double drug treatment group of gossypol and phenformin. However, in particular, it was confirmed that in the case of OVCAR3 cell line, in the triple drug treatment group in which mixing gossypol, phenformin, and cisplatin were mixed, the cell proliferation level was significantly suppressed and the cell number was reduced to exhibit an effect of killing the cells, compared to the case of single or double drug treatment with each anticancer agent, and thus it was confirmed that cisplatin can exhibit a synergistic effect of anticancer action when mixed with gossypol and phenformin (FIG. 6A). In contrast, as shown in FIGS. 6B and 6C, it was confirmed that since paclitaxel (FIG. 6B) and irinotecan (FIG. 6C) in the triple drug treatment group show only an effect of inhibiting cell proliferation in a level similar to that of the double drug treatment group, the synergistic effect of the anticancer action by treatment with triple drugs was not exhibited.

Example 7

Screening of Anticancer Agents that Show Synergistic Effects in Prostate Cancer by Combination Treatment with Gossypol and Phenformin In order to select a combination capable of exhibiting a synergistic effect of anticancer action on prostate cancer, doxorubicin, docetaxel and irinotecan as candidate anticancer agents in addition to gossypol and phenformin were selected as each subject.

Specifically, PC3 cell line or DU145 cell line as the prostate cancer cell line was each cultured, and the same method as in [Example 1] was performed and it was confirmed whether the synergistic effect of the anticancer action was exhibited by the mixed administration of the anticancer agents disclosed in [Table 19] to [Table 21] as cell growth in the prostate cancer cells is inhibited, through SRB analysis.

TABLE 19

Figure 7A:
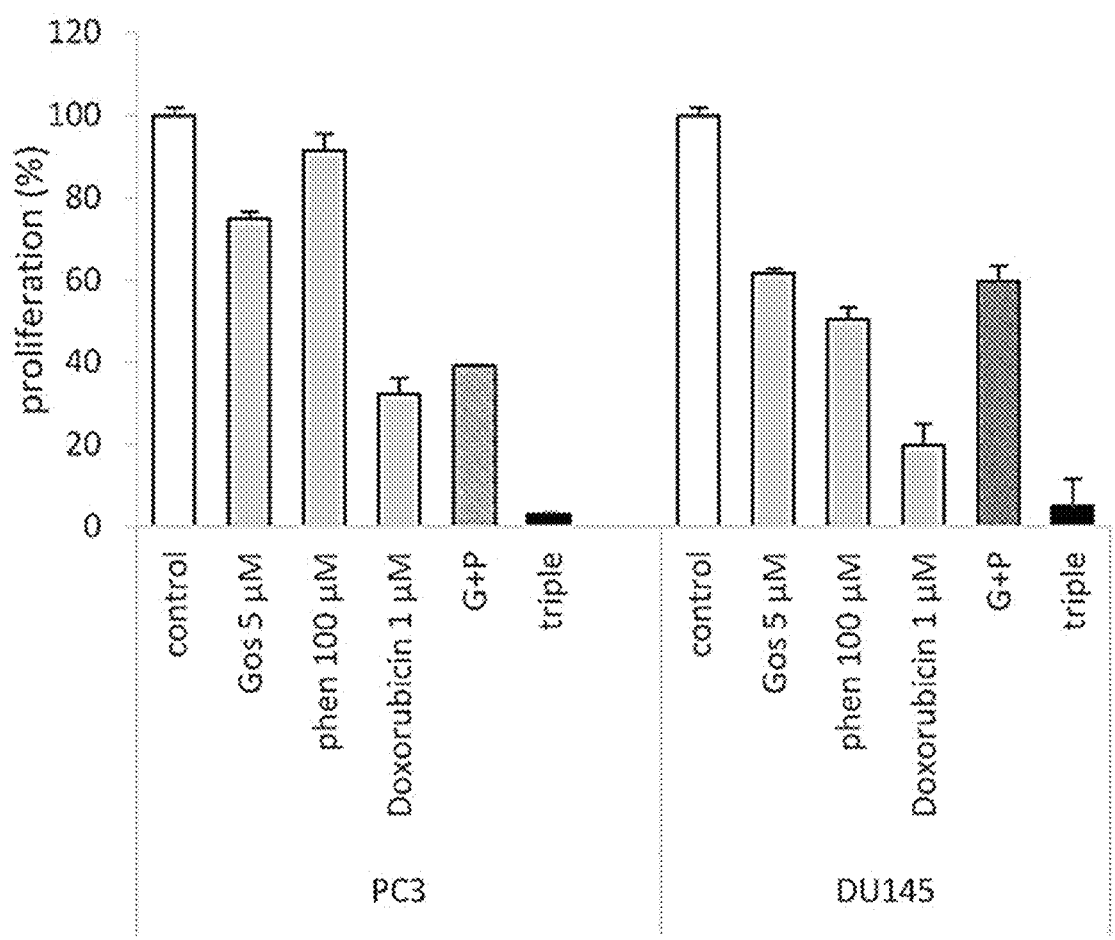
FIGS. 7A to 7C show a synergistic effect of inhibiting cell proliferation by a combination treatment of gossypol, phenformin, and an anticancer agent (doxorubicin, docetaxel, or irinotecan) in a prostate cancer cell line.

Design of a triple drug treatment group experiment containing doxorubicin (FIG. 7A)

| Number | Sample name | Anticancer agent (μM) | | |
|---|---|---|---|---|
| 1 | Single treatment group with gossypol | Gossypol (5 μM) | — | — |
| 2 | Single treatment group with phenformin | — | Phenformin (100 μM) | — |
| 3 | Single treatment group with doxorubicin | — | — | Doxorubicin (1 nM) |
| 4 | Double drug treatment group | Gossypol (5 μM) | Phenformin (100 μM) | — |
| 5 | Triple drug treatment group | Gossypol (5 μM) | Phenformin (100 μM) | Doxorubicin (1 nM) |

TABLE 20

Figure 7B:
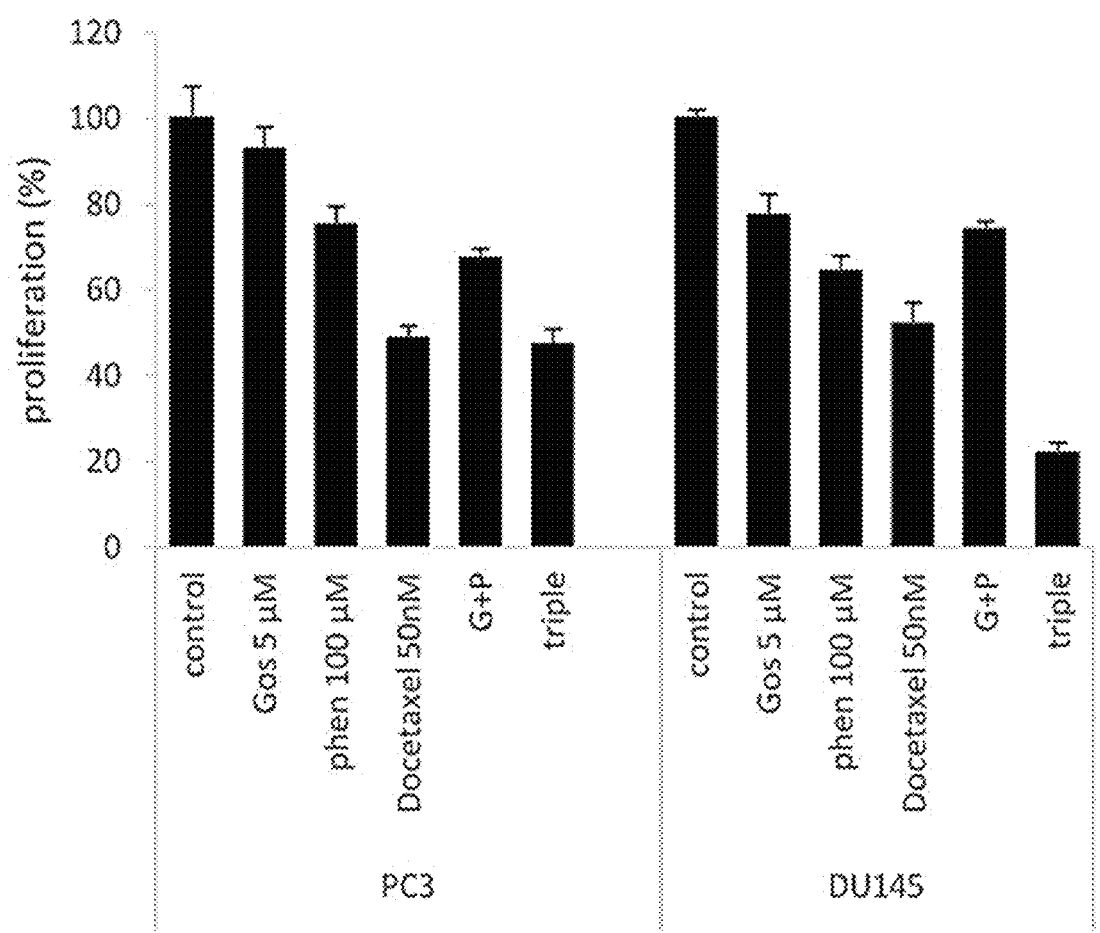

Design of a triple drug treatment group experiment containing docetaxel (FIG. 7B)

| Number | Sample name | Anticancer agent (μM) | | |
|---|---|---|---|---|
| 1 | Single treatment group with gossypol | Gossypol (5 μM) | — | — |
| 2 | Single treatment group with phenformin | — | Phenformin (100 μM) | — |
| 3 | Single treatment group with docetaxel | — | — | Docetaxel (50 nM) |
| 4 | Double drug treatment group | Gossypol (5 μM) | Phenformin (100 μM) | — |
| 5 | Triple drug treatment group | Gossypol (5 μM) | Phenformin (100 μM) | Docetaxel (50 nM) |

TABLE 21

Figure 7C:
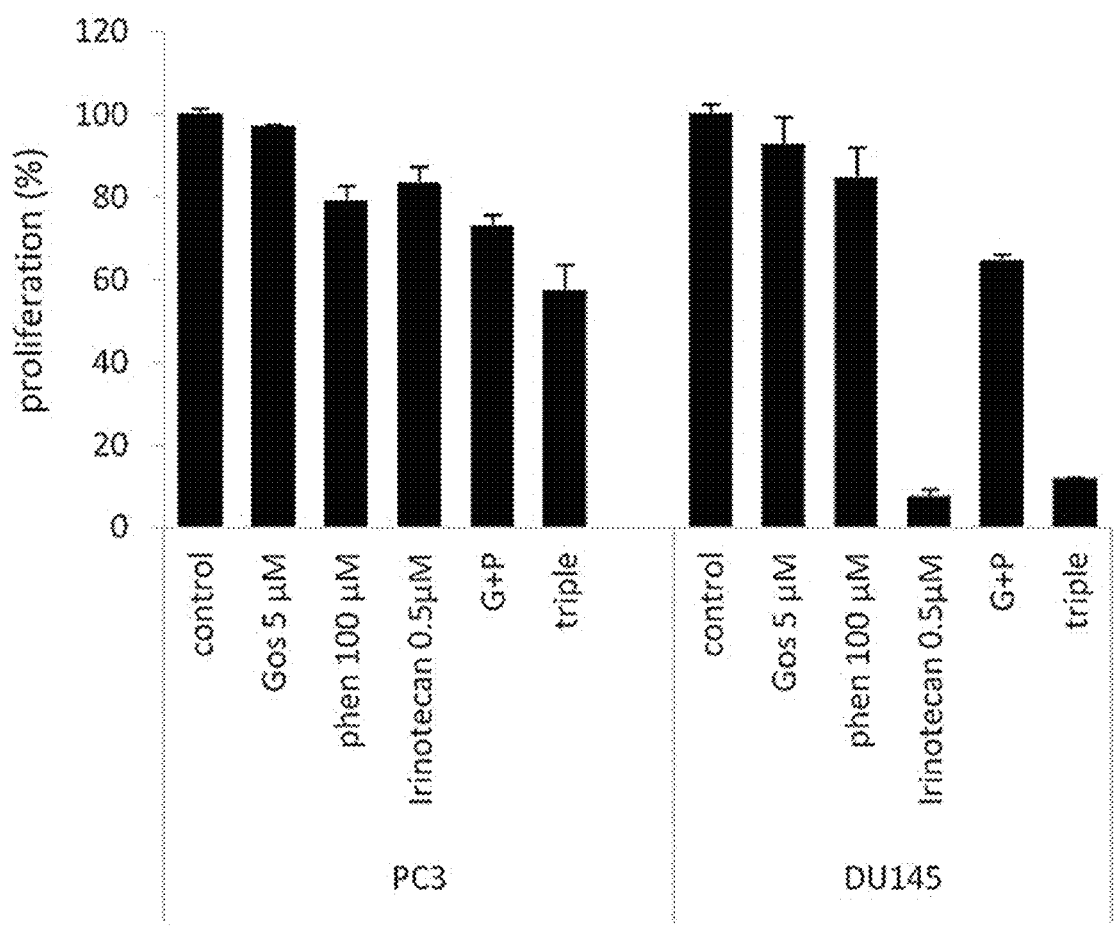

Design of a triple drug treatment group
experiment containing irinotecan (FIG. 7C)

| Number | Sample name | Anticancer agent (μM) | | |
|---|---|---|---|---|
| 1 | Single treatment group with gossypol | Gossypol (5 μM) | — | — |
| 2 | Single treatment group with phenformin | — | Phenformin (100 μM) | — |
| 3 | Single treatment group with irinotecan | — | — | Irionotecan (0.5 μM) |
| 4 | Double drug treatment group | Gossypol (5 μM) | Phenformin (100 μM) | — |
| 5 | Triple drug treatment group | Gossypol (5 μM) | Phenformin (100 μM) | Irionotecan (0.5 μM) |

As a result, first, as shown in FIG. 7A, it was confirmed that the proliferation of cancer cells could be inhibited at a significant level when each cell of prostate cancer was treated with a single treatment group of gossypol, phenformin, or doxorubicin and a double drug treatment group of gossypol and phenformin. However, in particular, it was confirmed that in the triple drug treatment group in which gossypol, phenformin, and doxorubicin were mixed, the cell proliferation level was significantly suppressed compared to the case of single or double drug treatment with each anticancer agent, and thus it was confirmed that doxorubicin can exhibit a synergistic effect of anticancer action when mixed with gossypol and phenformin (FIG. 7A). In contrast, as shown in FIGS. 7B and 7C, it was confirmed that since docetaxel (FIG. 7B) and irinotecan (FIG. 7C) in the triple drug treatment group show only an effect of inhibiting cell proliferation in a level similar to that of the double drug treatment group, the synergistic effect of the anticancer action by treatment with triple drugs was not exhibited.

Example 8

Screening of Anticancer Agents that Show Synergistic Effects in Liver Cancer by Combination Treatment with Gossypol and Phenformin In order to select a combination capable of exhibiting a synergistic effect of anticancer action on liver cancer, cisplatin and sorafenib as candidate anticancer agents in addition to gossypol and phenformin were selected as each subject.

Specifically, SNU449 or Huh7 cell line as the liver cancer cell line was each cultured, and the same method as in [Example 1] was performed and it was confirmed whether the synergistic effect of the anticancer action was exhibited by the mixed administration of the anticancer agents disclosed in [Table 22] and [Table 23] as cell growth in the liver cancer cells is inhibited, through SRB analysis.

TABLE 22

Figure 8A:
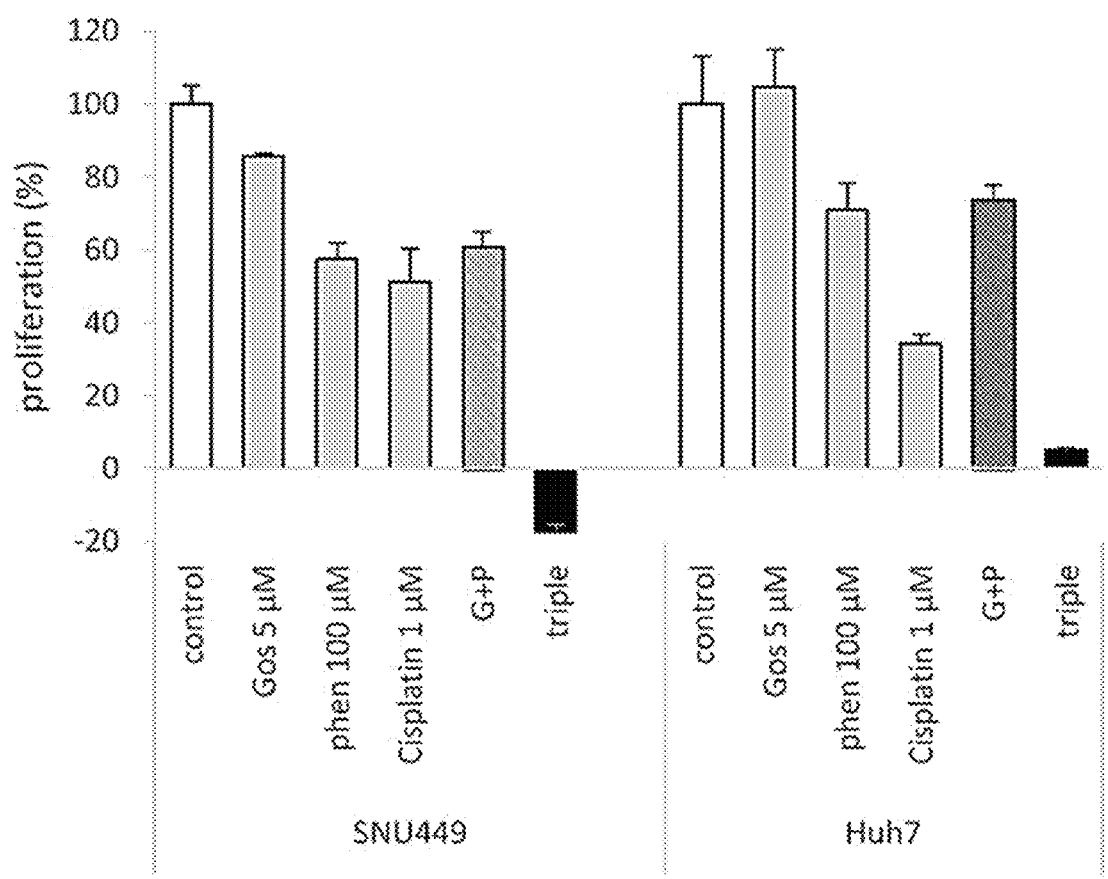
FIGS. 8A and 8B show a synergistic effect of inhibiting cell proliferation by a combination treatment of gossypol, phenformin, and an anticancer agent (cisplatin or sorafenib) in a liver cancer cell line.

Design of a triple drug treatment group
experiment containing cisplatin (FIG. 8A)

| Number | Sample name | Anticancer agent (μM) | | |
|---|---|---|---|---|
| 1 | Single treatment group with gossypol | Gossypol (5 μM) | — | — |
| 2 | Single treatment group with phenformin | — | Phenformin (100 μM) | — |
| 3 | Single treatment group with cisplatin | — | — | Cisplatin (1 μM) |
| 4 | Double drug treatment group | Gossypol (5 μM) | Phenformin (100 μM) | — |
| 5 | Triple drug treatment group | Gossypol (5 μM) | Phenformin (100 μM) | Cisplatin (1 μM) |

TABLE 23

Figure 8B:
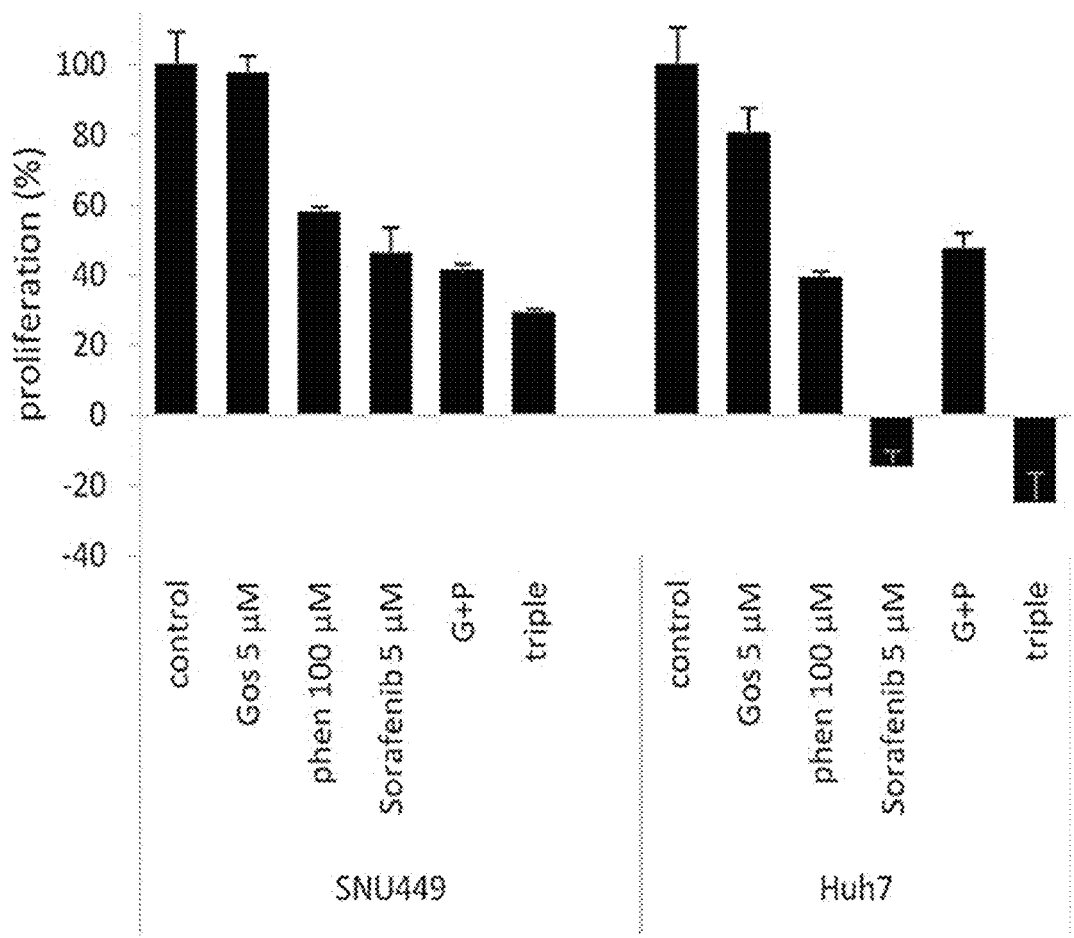

Design of a triple drug treatment group
experiment containing sorafenib (FIG. 8B)

| Number | Sample name | Anticancer agent (μM) | | |
|---|---|---|---|---|
| 1 | Single treatment group with gossypol | Gossypol (5 μM) | — | — |
| 2 | Single treatment group with phenformin | — | Phenformin (100 μM) | — |
| 3 | Single treatment group with sorafenib | — | — | Sorafenib (5 μM) |
| 4 | Double drug treatment group | Gossypol (5 μM) | Phenformin (100 μM) | — |
| 5 | Triple drug treatment group | Gossypol (5 μM) | Phenformin (100 μM) | Sorafenib (5 μM) |

As a result, first, as shown in FIG. 8A, it was confirmed that the proliferation of cancer cells could be inhibited at a significant level when each prostate cancer cell was treated with both a single treatment group of gossypol, phenformin, or cisplatin and a double drug treatment group of gossypol and phenformin. However, in particular, it was confirmed that in the case of OVCAR3 cell line, in the triple drug treatment group in which gossypol, phenformin, and cisplatin were mixed, the cell proliferation level was significantly suppressed and the cell number was reduced to exhibit an effect of killing the cells, compared to the case of single or double drug treatment with each anticancer agent, and thus it was confirmed that cisplatin can exhibit a synergistic effect of anticancer action when mixed with gossypol and phenformin (FIG. 8A). In contrast, as shown in FIGS. 8B, it was confirmed that since sorafenib in triple drug treatment group shows only an effect of inhibiting cell proliferation in a level similar to that of the double drug treatment group, the synergistic effect of the anticancer action by treatment with triple drugs was not exhibited.

Example 9

Confirmation of Anticancer Effect in Non-Small Cell Lung Cancer Model by Combination Administration with Gossypol and Phenformin It was found that treatment of the triple drug obtained by mixing the anticancer agents selected in the above examples with gossypol and phenformin can exhibit a synergistically elevated cancer cell growth inhibitory effect compared to treatment of each alone (In vitro), and thus it was confirmed whether the same synergistic effect could be exhibited at the in vivo level afterwards.

First, in order to make a lung cancer mouse model, 6 to 8 week old Balb/c-nu mice (Central Lab. Animal, Highland Heights, KY, USA) were prepared. In addition, 7.5×10$^6$ A549 cell line was cultured, and was injected subcutaneously to the prepared mice with a 1 ml syringe. Mice were reared for 1 week and divided into 4 groups of 8 mice each, and these were used as a control group or an experimental group as defined in [Table 24] and [Table 25]. The solvent or drug was orally administered to the mice of the solvent control group, the double drug treatment group, and the triple drug treatment group once a day, 6 days per week, and while administering intravenously irinotecan to the mice of the single treatment group with irinotecan once a day, 1 day per week, the mice were reared in the same environment for a total of 49 days. While breeding, the average was obtained by checking the weight and size of the tumor of the mouse group every 7 days. After injection of lung cancer cells, the initial tumor size was specified using a calliper. The tumor volume was calculated according to the following [Equation 1].

$$\text{volume}(mm^3) = \frac{\text{long diameter} \times \text{short diameter}^2}{2} \quad \text{[Equation 1]}$$

TABLE 24

| Number | Name | Composition for administration | | |
|---|---|---|---|---|
| 1 | Solvent control group | Solvent (5% DMSO, 5% cremophor in PBS, 100 μl) | | |
| 2 | Double drug administration group | Gossypol (80 mg/kg/100 μl) | Phenformin (100 mg/kg/100 μl) | — |
| 3 | Single administration group with irinotecan | — | — | Irinotecan (20 mg/kg/100 μl) |
| 4 | Triple drug administration group | Gossypol (80 mg/kg/100 μl) | Phenformin (100 mg/kg/100 μl) | Irinotecan (20 mg/kg/100 μl) |

TABLE 25

| Number | Name | Composition for administration | | |
|---|---|---|---|---|
| 1 | Solvent control group | Solvent (5% DMSO, 5% cremophor in PBS, 100 μl) | | |
| 2 | Double drug administration group | Gossypol (80 mg/kg/100 μl) | Phenformin (100 mg/kg/100 μl) | — |
| 3 | Single administration group with gemcitabine | — | — | Gemcitabine(40 mg/kg/100 μl) |
| 4 | Triple drug administration group | Gossypol (80 mg/kg/100 μl) | Phenformin (100 mg/kg/100 μl) | Gemcitabine (40 mg/kg/100 μl) |

Figure 9A:
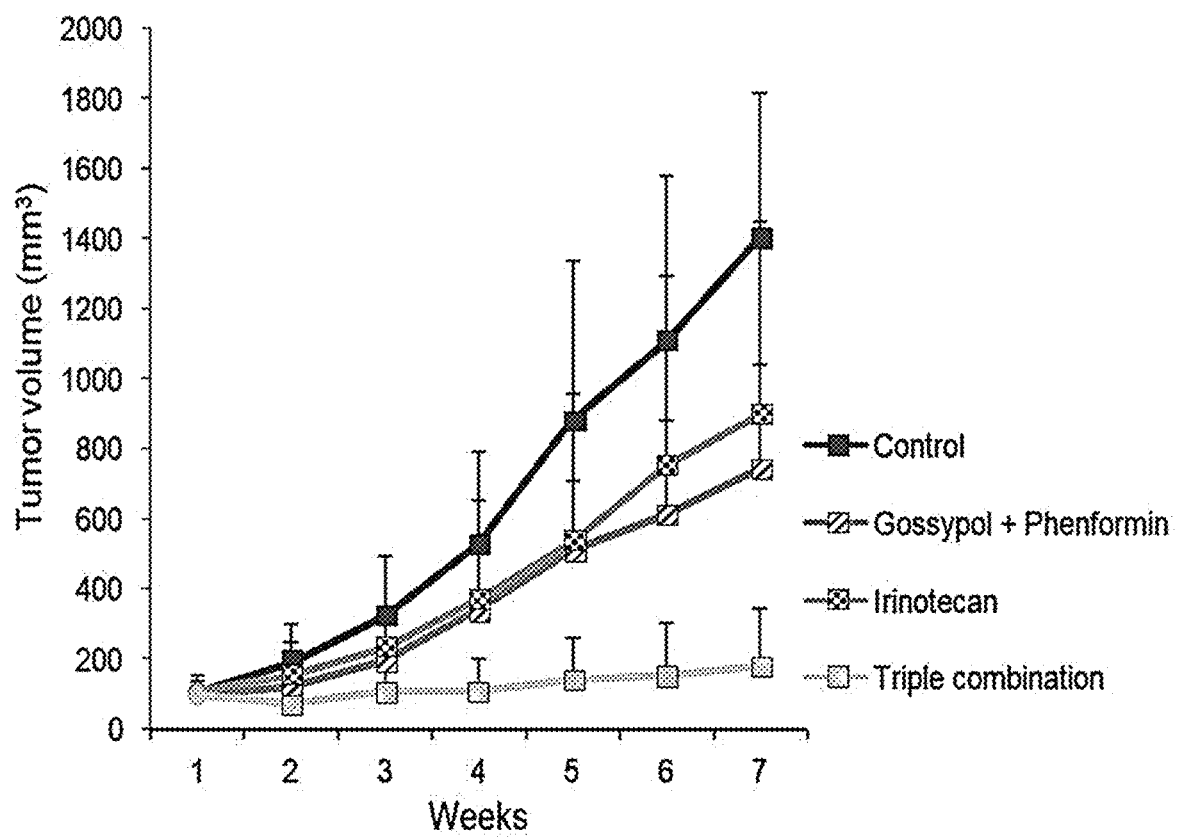
FIG. 9A is a diagram illustrating a change in tumor size according to the number of days of breeding.
Figure 9B:
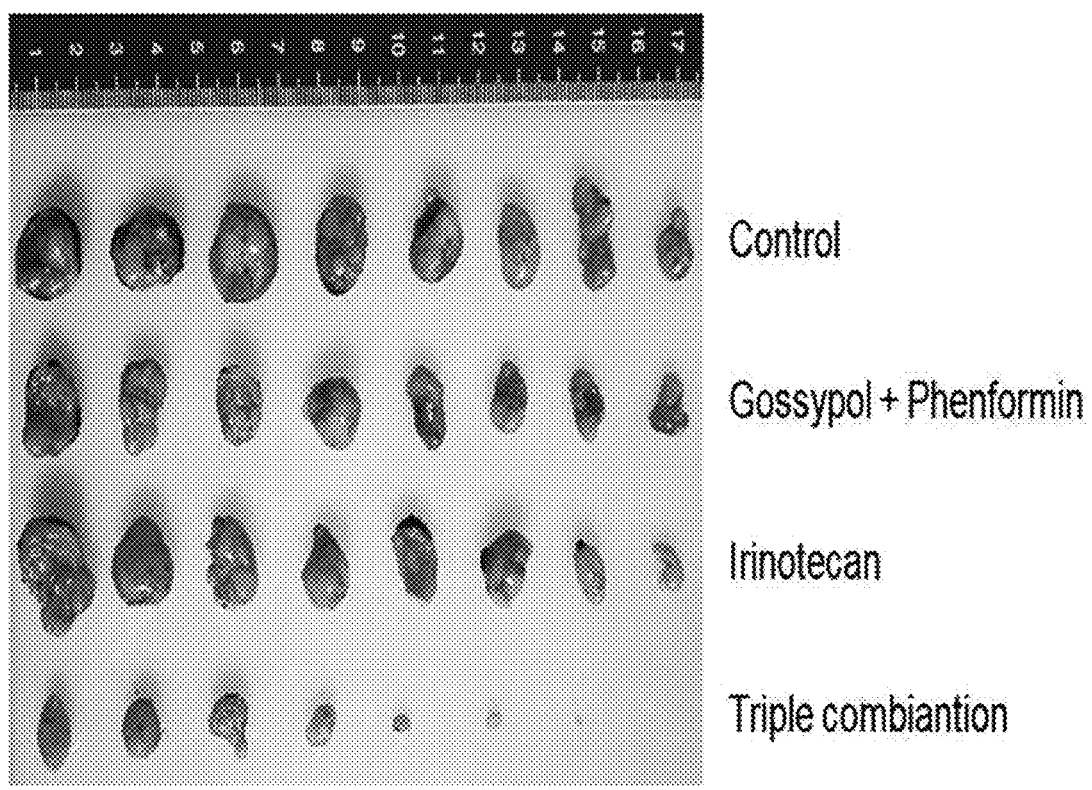
FIG. 9B is a picture comparing tumor size in each drug administration group after completion of breeding.
Figure 9B:
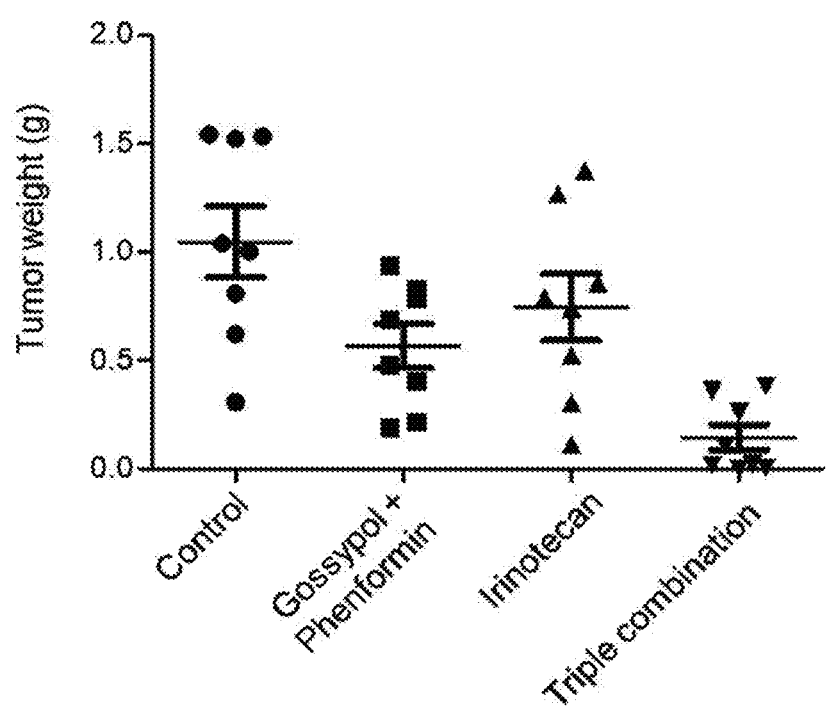

As a result, it was confirmed from FIG. 9 that in the mouse model in which lung cancer tumors grow in the experimental group to which irinotecan was administered, the tumor volume and weight showed a significant difference according to the drug treatment. Among the mouse models transplanted with lung cancer tumors through lung cancer cell line injection, the tumor volume continued to increase in the solvent control group to which no drug was administered. In contrast, it was confirmed that the double drug administration group of gossypol and phenformin and the single administration group with irinotecan showed a tendency to slightly decrease the scale of the increase in tumor volume, and the levels were similar to each other. However, the effect of inhibiting the increase in tumor volume was more synergistic than that in the case of a combination administration with triple drugs of gossypol, phenformin, and irinotecan, and it was confirmed that the tumor did not increase significantly even after breeding a lung cancer mouse model for a total of 7 weeks (FIG. 9A). After the end of breeding, even when the mice were sacrificed and the tumor size and weight were compared, it was confirmed that the tumor weight and size of the triple drug administration group were significantly reduced compared to other controls and administration groups (FIGS. 9B and 9C).

Figure 10:
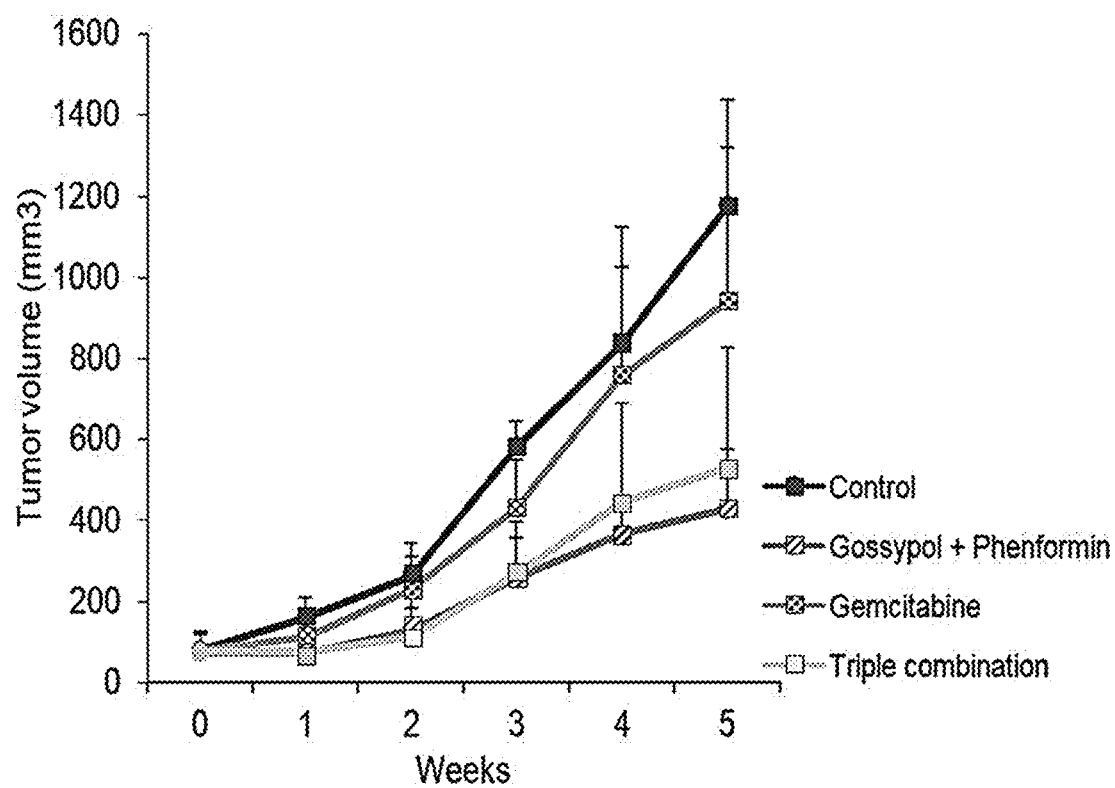
FIG. 10 is a diagram illustrating a change in tumor size in a triple combination group of gossypol, phenformin, and gemcitabine in a mouse model of non-small cell lung cancer.

On the other hand, as shown in FIG. 10, in the case of the gemcitabine-administered experimental group, the anticancer synergistic effect of the triple drug administration was not observed (FIG. 10). It was confirmed that the single administration group with gemcitabine had tumor growth at a level similar to that of the solvent administration group, and showed a significant tumor growth inhibitory effect in the double drug administration group with gossypol and phenformin. In addition, it was confirmed that even though the triple drug was administered by adding gemcitabine to gossypol and phenformin, the growth level of the tumor size was similar to that of the double drug administration group.

Example 10

Confirmation of Anticancer Effect in Melanoma Model by Combination Administration with Gossypol and Phenformin In order to once again confirm the synergistic effect of the combination administration of the anticancer agent of the present disclosure in vivo, a combination of anticancer agents was administered to a mouse model xenografted with melanoma.

Specifically, the melanoma mouse model was prepared by the same method as the method of preparing the lung cancer mouse model in [Example 9], except that a melanoma model was prepared by xenografting A375 cells. Then, the prepared melanoma mouse model was used as a control group or an experimental group as defined in the following [Table 26].

TABLE 26

| Number | Name | Composition for administration | | |
|---|---|---|---|---|
| 1 | Solvent control group | Solvent (5% DMSO, 5% cremophor in PBS, 100 μl) | | |
| 2 | Double drug administration group | Gossypol (80 mg/kg/100 μl) | Phenformin (100 mg/kg/100 μl) | — |
| 3 | Single administration group with vemurafenib | — | — | Vemurafenib (30 mg/kg/100 μl) |
| 4 | Triple drug administration group | Gossypol (80 mg/kg/100 μl) | Phenformin (100 mg/kg/100 μl) | Vemurafenib (30 mg/kg/100 μl) |

Figure 11A:
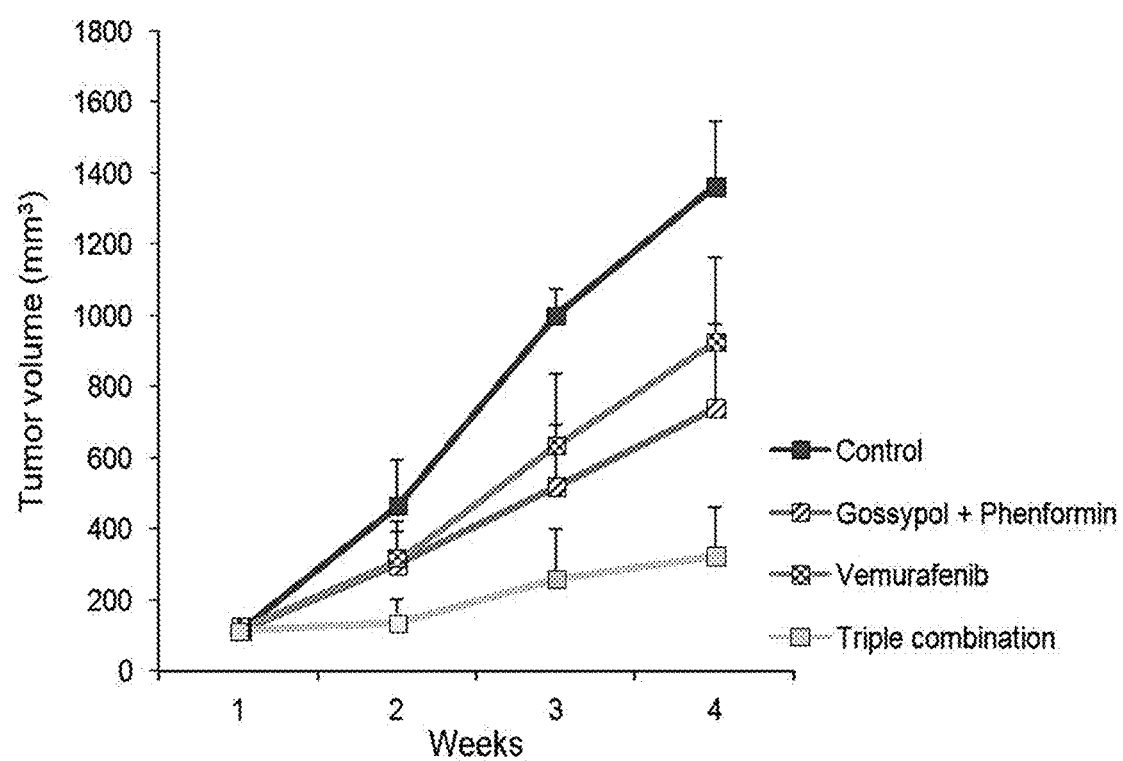
Figure 11B:
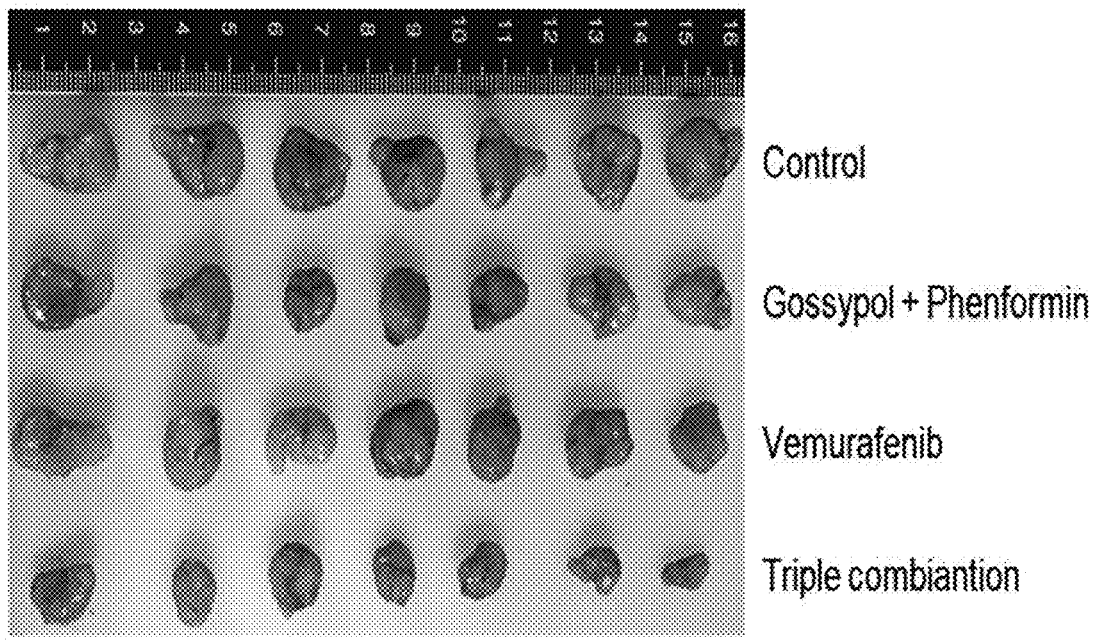
Figure 11C:
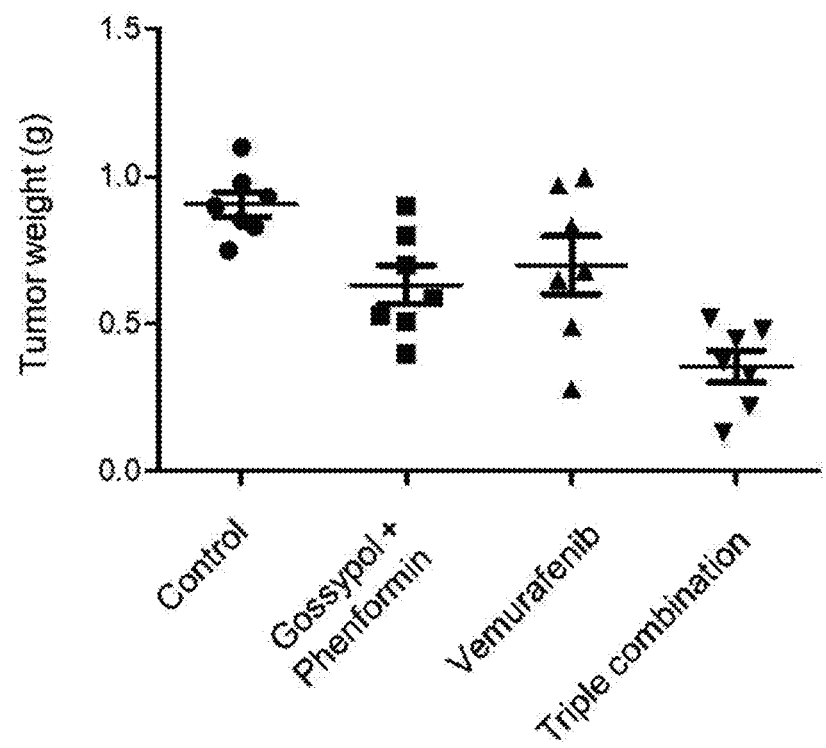

As a result, as shown in FIGS. 11A-11C, it was confirmed that the tumor volume and weight in a mouse model in which a tumor grows due to xenograft of a melanoma cell line showed a significant difference according to treatment with an anticancer agent. Compared to the solvent control group, the double drug administration group with gossypol and phenformin and the single administration group with vemurafenib showed a tendency to slightly decrease the scale of increase in tumor volume. However, it was confirmed that the effect of inhibiting the increase in tumor volume exhibited a more synergistic effect than that in the case of a combination administration of the triple drugs with gossypol, phenformin, and vemurafenib (FIG. 11A). After the end of breeding, even when the mice were sacrificed and the tumor size and weight were compared, it was confirmed that the tumor weight and size of the triple drug administration group were significantly reduced compared to other controls and administration groups (FIGS. 11B and 11C).

Example 11

Confirmation of Anticancer Effect in Gastric Cancer Model by Combination Administration with Gossypol and Phenformin In order to once again confirm the synergistic effect of the combination administration of the anticancer agent of the present disclosure in vivo, a combination of anticancer agents was administered to a mouse model xenografted with gastric cancer.

Specifically, the mouse model with the gastric cancer was prepared by the same method as the method of preparing the lung cancer mouse model in [Example 9], except that the mouse model with the gastric cancer was prepared by xenografting SNU638 cells ($1.5 \times 10^7$). Then, the prepared mouse model with the gastric cancer was used as a control group or an experimental group as defined in the following [Table 27].

Figure 12A:
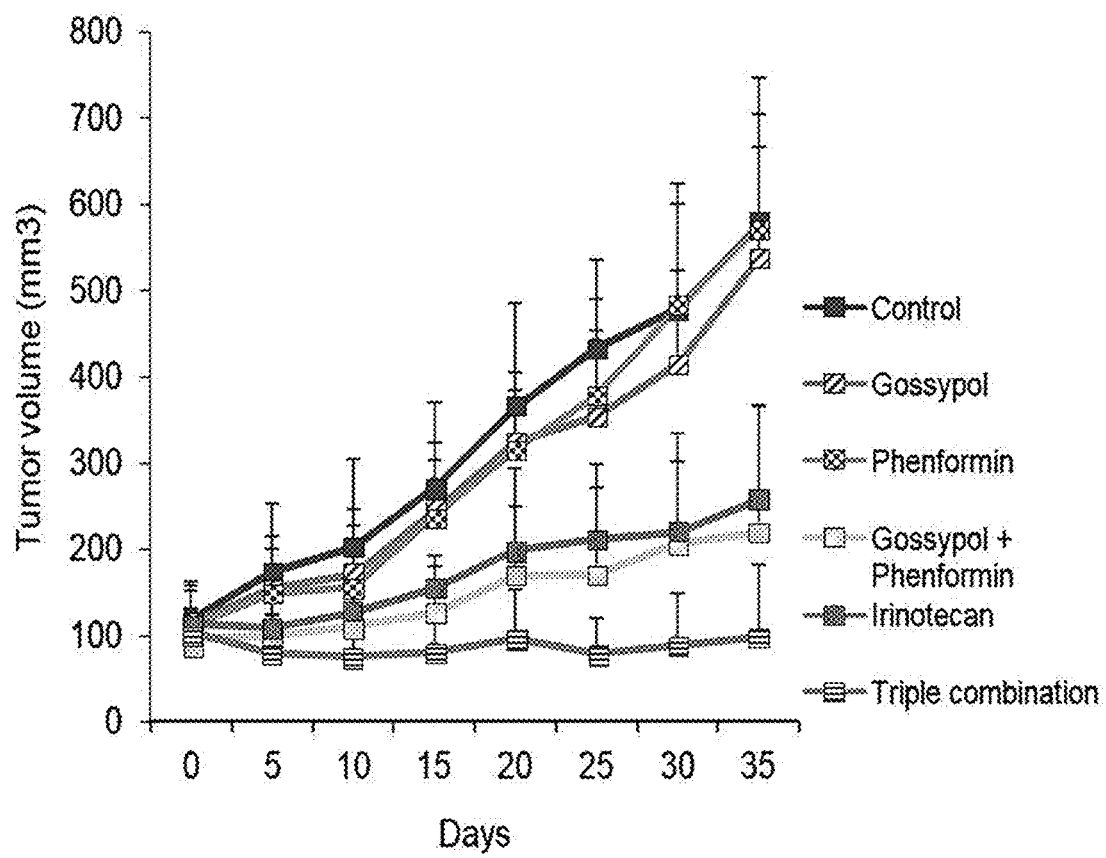
Figure 12B:
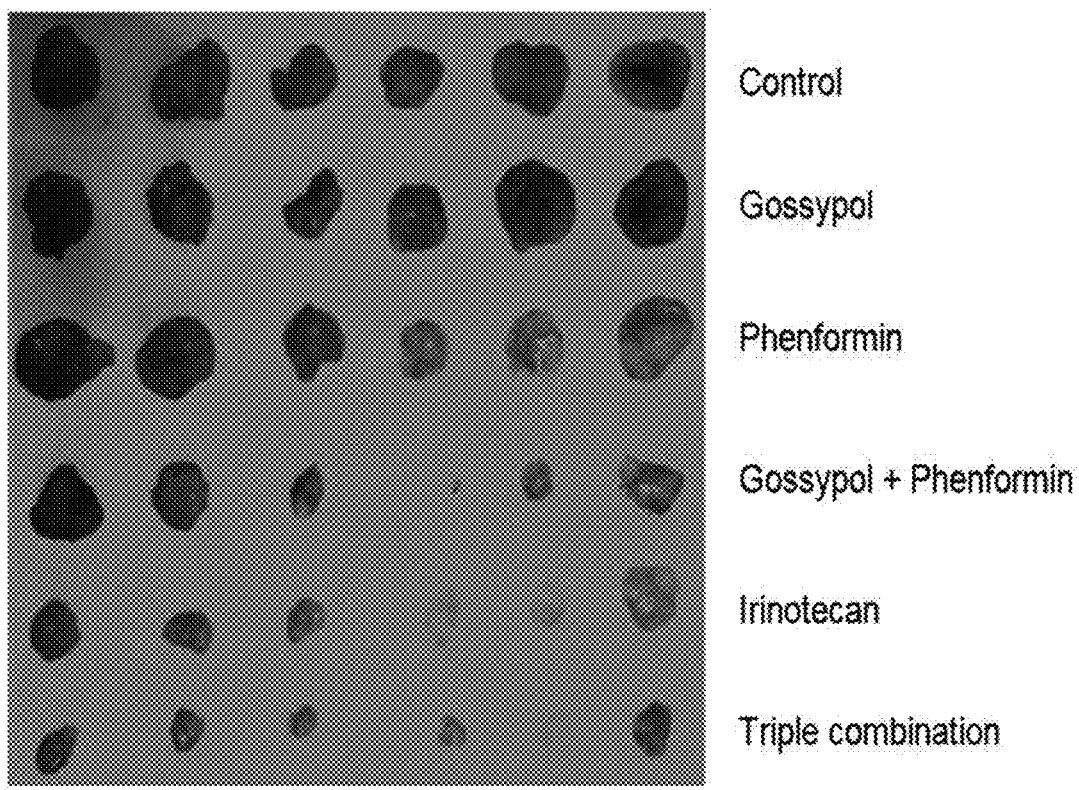
Figure 12C:
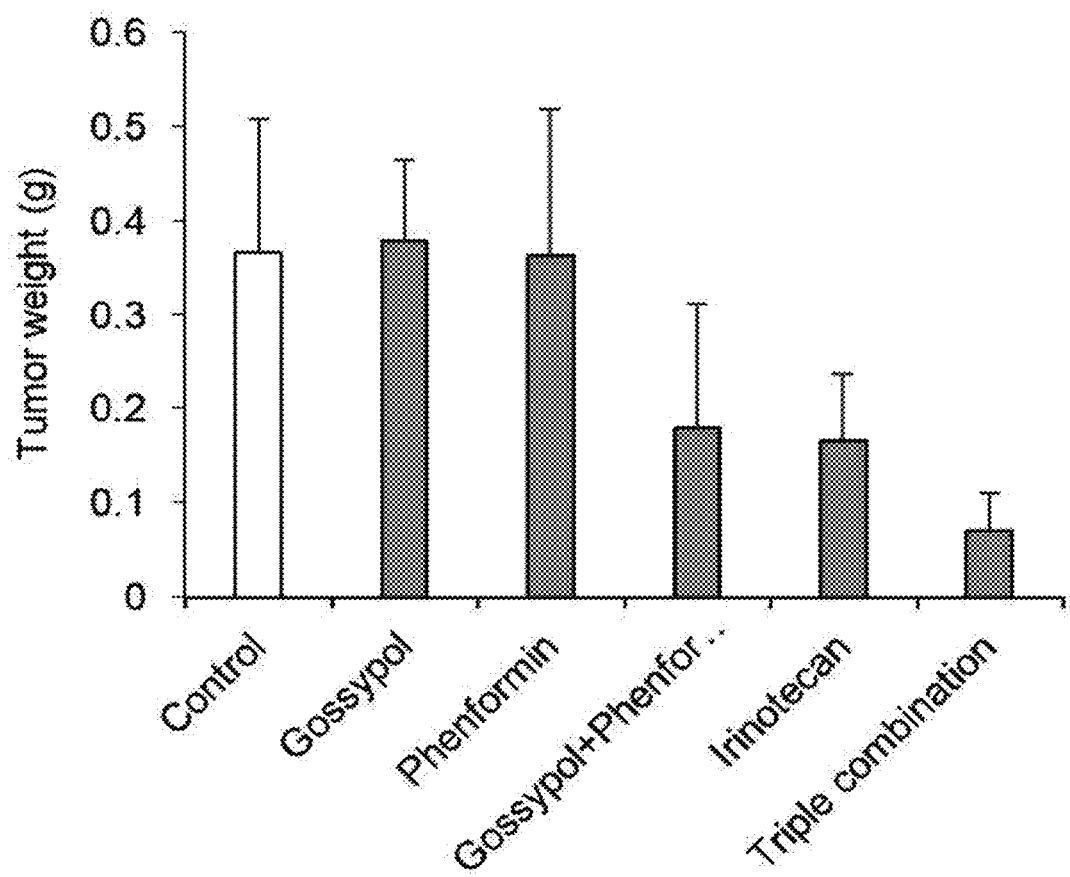

As a result, as shown in FIGS. 12A-12C, it was confirmed that the solvent control group, the single administration group with gossypol, and the single administration group with phenformin were a level similar to levels of tumor growth of gastric cancer (FIGS. 12A and 12B). In contrast, the double drug administration group and the administration group with irinotecan significantly decreased the level of tumor growth. In addition, it was confirmed that tumor growth hardly occurred in the triple drug administration group in which gossypol, phenformin, and irinotecan were all mixed and administered in combination. After a bleeding for a total of thirty-five (35) days, even when the mice were sacrificed and the tumor size and weight were compared, it was confirmed that the tumor weight and size of the triple drug administration group were significantly reduced compared to other controls and administration groups (FIGS. 12B and 12C).

Example 12

Confirmation of Anticancer Effect in Prostate Cancer Model by Combination Administration with Gossypol and Phenformin In order to once again confirm the synergistic effect of the combination administration of the anticancer agent of the present disclosure in vivo, a combination of anticancer agents was administered to a mouse model xenografted with prostate cancer.

Specifically, the mouse model with the prostate cancer was prepared the same as the method of preparing the lung cancer mouse model in [Example 9], but the mouse model with the prostate cancer was prepared by xenografting PC3 cells ($5 \times 10^6$). Then, the prepared mouse model with the prostate cancer was used as a control group or an experimental group as defined in the following [Table 28].

TABLE 27

| Number | Name | Composition for administration | | |
|---|---|---|---|---|
| 1 | Solvent control group | Solvent (5% DMSO, 5% cremophor in PBS, 100 μl) | | |
| 2 | Single administration group with gossypol | Gossypol (80 mg/kg/100 μl) | — | — |
| 3 | Single administration group with phenformin | — | Phenformin (100 mg/kg/100 μl) | — |
| 4 | Double drug administration group | Gossypol (80 mg/kg/100 μl) | Phenformin (100 mg/kg/100 μl) | — |
| 5 | Single administration group with irinotecan | — | — | Irinotecan (30 mg/kg/100 μl) |
| 6 | Triple drug administration group | Gossypol (80 mg/kg/100 μl) | Phenformin (100 mg/kg/100 μl) | Irinotecan (30 mg/kg/100 μl) |

TABLE 28

| Number | Name | Composition for administration | | |
|---|---|---|---|---|
| 1 | Solvent control group | Solvent (5% DMSO, 5% cremophor in PBS, 100 μl) | | |
| 2 | Double drug administration group | Gossypol (80 mg/kg/100 μl) | Phenformin (100 mg/kg/100 μl) | — |
| 3 | Single administration group with doxorubicin | — | — | Doxorubicin (5 mg/kg/100 μl) |
| 4 | Triple drug administration group | Gossypol (80 mg/kg/100 μl) | Phenformin (100 mg/kg/100 μl) | Doxorubicin (5 mg/kg/100 μl) |

Figure 13A:
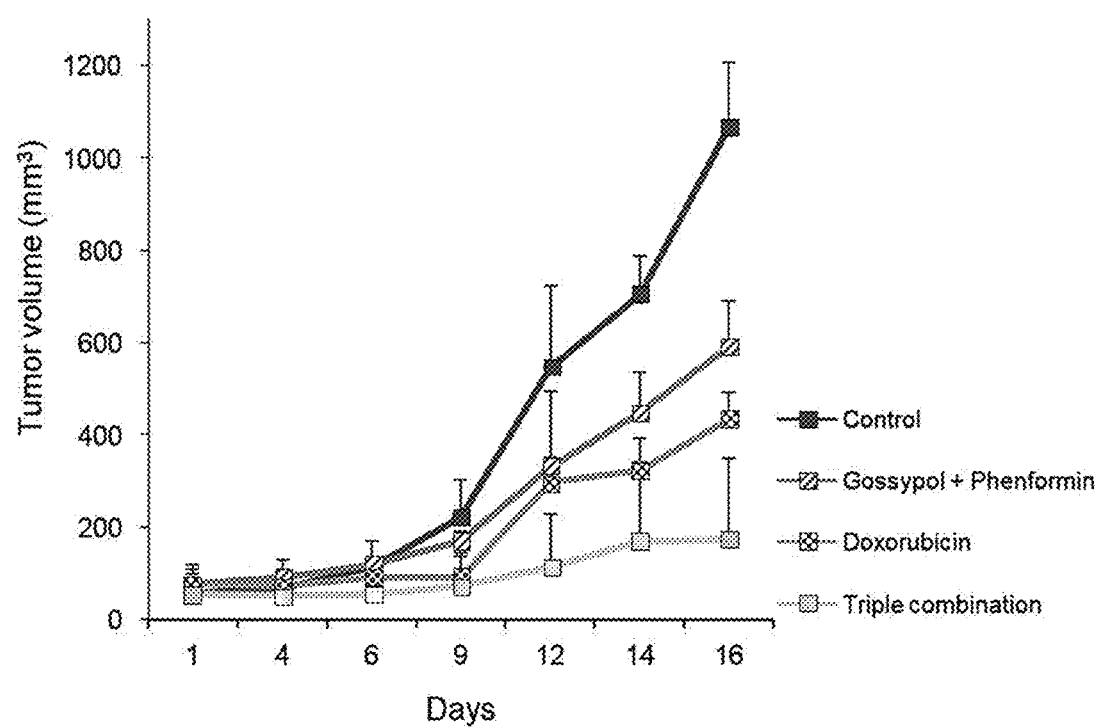
Figure 13B:
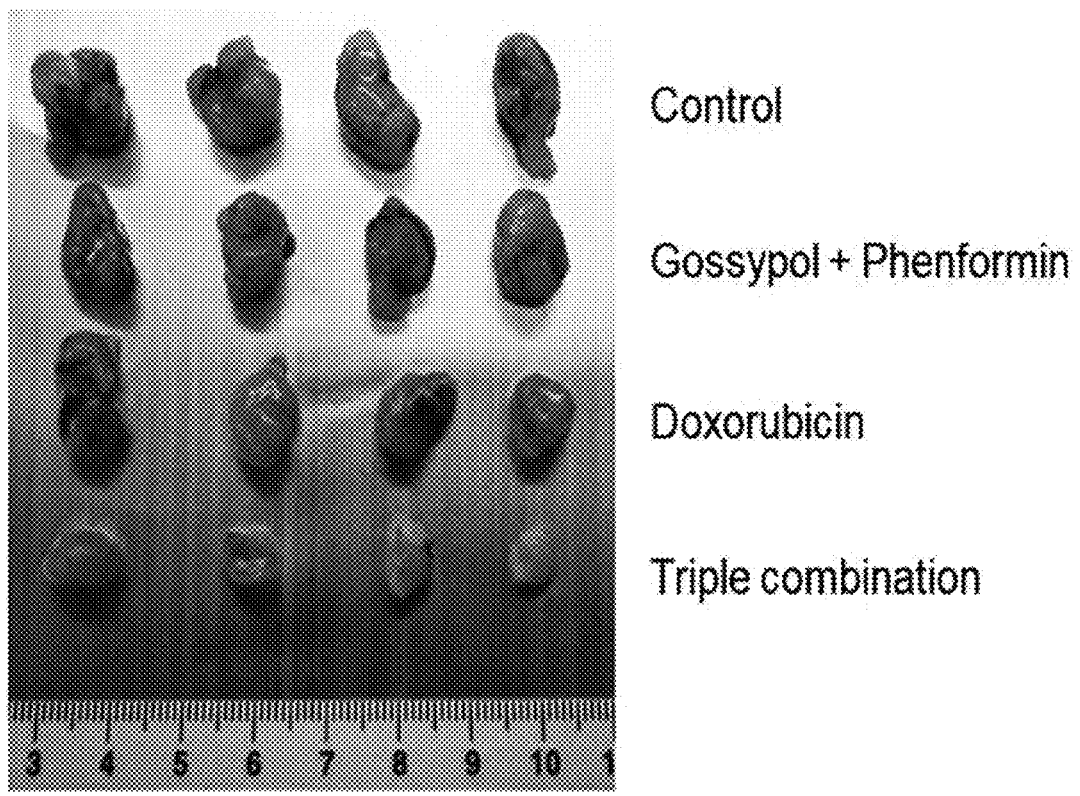
Figure 13C:
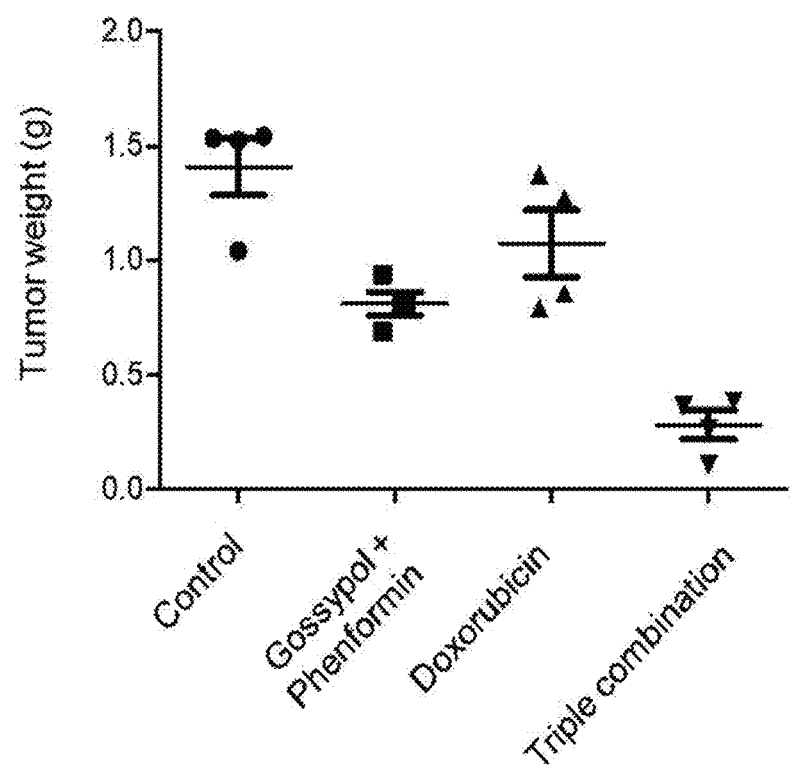

As a result, as shown in FIGS. 13A-13C, it was confirmed that the double drug administration group and the single administration group with doxorubicin significantly inhibited tumor growth compared to the solvent control group, and also, that the tumor growth level in the triple drug administration group was the lowest (FIGS. 13A and 13B). After a bleeding for a total of 16 days, even when the mice were sacrificed and the tumor size and weight were compared, it was confirmed that the tumor weight and size of the triple drug administration group were significantly reduced compared to other controls and administration groups (FIGS. 13B and 13C).

As described above, in the present disclosure, an anticancer agent combination capable of exhibiting a synergistic activity of anticancer effect by a combination administration with gossypol and phenformin was selected. Anticancer agent combinations capable of exhibiting a synergistic effect are different depending on the carcinoma, and summarized as shown in [Table 29] below.

TABLE 29

| Drug that exhibits synergistic effects when administered in combination with gossypol and phenformin | | |
|---|---|---|
| Carcinoma | Presence of synergistic effects | Absence of synergistic effects |
| Renal cell carcinoma | Sorafenib | Sunitinib, Pazopanib |
| Melanoma | Vemurafenib | Cisplatin, Oxaliplatin |
| Colon cancer | Irinotecan | Cisplatin, Capecitabine |
| Lung cancer | Irinotecan | Cisplatin, 5-FU |
| Breast cancer | Paclitaxel | Cisplatin, Doxorubicin |
| Ovarian cancer | Cisplatin | Paclitaxel, Irinotecan |
| Prostate cancer | Doxorubicin | Docetaxel, irinotecan |
| Liver cancer | Cisplatin | Sorafenib |
| Gastric cancer | Irinotecan | |

Industrial Applicability

The present inventors confirmed that the cancer cell proliferation inhibitory effect and the cancer metastasis inhibitory effect in various carcinomas were remarkably increased, and the growth of xenografted tumors in the mouse model was inhibited, when sorafenib, vemurafenib, irinotecan, cisplatin, paclitaxel, or doxorubicin are mixed together with gossypol and phenformin. Therefore, it is expected that the present disclosure will be widely used in the medical field.

The invention claimed is:

1. A method for treating cancer in a patient comprising administering to the patient a pharmaceutical composition comprising gossypol, phenformin and cisplatin as active ingredients, wherein the cancer is ovarian cancer or liver cancer.

2. The method of claim 1, wherein the pharmaceutical composition comprises gossypol, phenformin, and cisplatin mixed at a molar ratio of 0.1 to 10:10 to 500:1.

3. The method of claim 1, wherein the cancer includes a cancer stem cell.

4. A method for inhibiting cancer metastasis in a patient comprising administering to the patient a pharmaceutical composition comprising gossypol, phenformin and cisplatin as active ingredients, wherein the cancer is ovarian cancer or liver cancer.

5. The method of claim 4, wherein the pharmaceutical composition comprises gossypol, phenformin, and cisplatin mixed at a molar ratio of 0.1 to 10:10 to 500:1.

6. The method of claim 4, wherein the cancer includes a cancer stem cell.

7. A method for treating cancer or inhibiting cancer metastasis in a patient, comprising administering to the patient gossypol, phenformin and cisplatin, wherein the cancer is ovarian cancer or liver cancer.

8. The method of claim 7, wherein the gossypol, the phenformin, and the cisplatin are administered in a molar ratio of 0.1 to 10:10 to 500:1.

9. The method of claim 7, wherein the cancer includes a cancer stem cell.

10. The method of claim 1, wherein the cancer is ovarian cancer.

11. The method of claim 1, wherein the cancer is liver cancer.

12. The method of claim 4, wherein the cancer is ovarian cancer.

13. The method of claim 4, wherein the cancer is liver cancer.

14. The method of claim 7, wherein the cancer is ovarian cancer.

15. The method of claim 7, wherein the cancer is liver cancer.

* * * * *